(12) United States Patent
Takada et al.

(10) Patent No.: US 10,910,578 B2
(45) Date of Patent: Feb. 2, 2021

(54) POLYCYCLIC COMPOUND AND ORGANIC ELECTROLUMINESCENCE DEVICE INCLUDING THE SAME

(71) Applicant: SAMSUNG DISPLAY CO., LTD., Yongin-si (KR)

(72) Inventors: Ichinori Takada, Yokohama (JP); Masatsugu Ueno, Yokohama (JP); Ichiro Imada, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 281 days.

(21) Appl. No.: 16/032,215

(22) Filed: Jul. 11, 2018

(65) Prior Publication Data

US 2019/0097157 A1 Mar. 28, 2019

(30) Foreign Application Priority Data

Sep. 26, 2017 (KR) .................. 10-2017-0124505

(51) Int. Cl.
*H01L 51/50* (2006.01)
*H01L 51/52* (2006.01)
(Continued)

(52) U.S. Cl.
CPC ........ *H01L 51/5036* (2013.01); *C07D 471/08* (2013.01); *C07D 471/18* (2013.01);
(Continued)

(58) Field of Classification Search
CPC .. C07D 471/08; C07D 471/18; C07D 519/00; C07F 7/0812; H01L 51/005;
(Continued)

(56) References Cited

U.S. PATENT DOCUMENTS 4,082,723 A * 4/1978 Mayer .................. C08K 5/005
524/83
9,812,652 B2 11/2017 Arai et al.
(Continued)

FOREIGN PATENT DOCUMENTS

JP 2002-270374 A 9/2002
JP 4189719 B2 12/2008
(Continued)

OTHER PUBLICATIONS

Bioorganic & Medicinal Chemistry Letters, vol. 21, No. 18, (2011), pp. 5289-5292. (Year: 2011).*
(Continued)

*Primary Examiner* — Dawn L Garrett
(74) *Attorney, Agent, or Firm* — Lewis Roca Rothgerber Christie LLP

(57) ABSTRACT

A polycyclic compound and an organic electroluminescence, the polycyclic compound being represented by the following Formula 1:

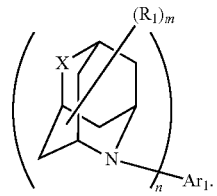

[Formula 1]

20 Claims, 2 Drawing Sheets

(51) Int. Cl.
  *H01L 51/00* (2006.01)
  *C07D 471/18* (2006.01)
  *C07F 7/08* (2006.01)
  *C07D 519/00* (2006.01)
  *C07D 471/08* (2006.01)

(52) U.S. Cl.
  CPC .......... *C07D 519/00* (2013.01); *C07F 7/0812* (2013.01); *H01L 51/005* (2013.01); *H01L 51/0059* (2013.01); *H01L 51/0067* (2013.01); *H01L 51/0072* (2013.01); *H01L 51/0073* (2013.01); *H01L 51/0074* (2013.01); *H01L 51/0094* (2013.01); *H01L 51/5024* (2013.01); *H01L 51/5092* (2013.01); *H01L 51/5096* (2013.01); *H01L 51/5218* (2013.01); *H01L 51/5234* (2013.01); *H01L 51/5064* (2013.01); *H01L 51/5072* (2013.01)

(58) Field of Classification Search
  CPC ............ H01L 51/0059; H01L 51/0067; H01L 51/0072; H01L 51/0073; H01L 51/0074; H01L 51/0094; H01L 51/5024; H01L 51/5036; H01L 51/5064; H01L 51/5072; H01L 51/5092; H01L 51/5096; H01L 51/5218; H01L 51/5234
  See application file for complete search history.

(56) References Cited

U.S. PATENT DOCUMENTS

2004/0209115 A1 10/2004 Thompson et al.
2005/0164032 A1 7/2005 Ise et al.

FOREIGN PATENT DOCUMENTS

| | | | |
|---|---|---|---|
| JP | 4408367 B2 | | 2/2010 |
| JP | 2015-034159 A | | 2/2015 |
| JP | 2016079360 A | * | 5/2015 |
| KR | 10-2016-0032020 A | | 3/2016 |
| KR | 10-1772990 B1 | | 8/2017 |
| WO | WO 03/055872 A1 | | 7/2003 |

OTHER PUBLICATIONS

J. Henkel et al., "General synthesis of N-Substituted 2-Azaadamantanes and Their 4,8-Disubstituted Derivatives", J. Org. Chem., 1981, 46(17), 3483.

Y. Tanaka et al., "Molecular dynamics study-guided identification of cyclic amine structures as novel hydrophobic tail components of hPPARγ agonists", Bioorganic & Medicinal Chemistry Letters 24(16), 2014, p. 4001-4005.

* cited by examiner

POLYCYCLIC COMPOUND AND ORGANIC ELECTROLUMINESCENCE DEVICE INCLUDING THE SAME

CROSS-REFERENCE TO RELATED APPLICATIONS

Korean Patent Application No. 10-2017-0124505, filed on Sep. 26, 2017, in the Korean Intellectual Property Office, and entitled: "Polycyclic Compound and Organic Electroluminescence Device Including the Same," is incorporated by reference herein in its entirety.

BACKGROUND

1. Field

Embodiments relate to a polycyclic compound and an organic electroluminescence device including the same.

2. Description of the Related Art

Development on an organic electroluminescence display as an image display is being actively conducted. An organic electroluminescence display is different from a liquid crystal display and is a self-luminescent display that accomplishes display by recombining holes and electrons injected from a first electrode and a second electrode in an emission layer and emitting light from a luminescent material which includes an organic compound in the emission layer.

An organic electroluminescence device may include, e.g., an organic electroluminescence device composed of a first electrode, a hole transport layer disposed on the first electrode, an emission layer disposed on the hole transport layer, an electron transport layer disposed on the emission layer, and a second electrode disposed on the electron transport layer. Holes are injected from the first electrode, and the injected holes move via the hole transport layer to be injected into the emission layer. Meanwhile, electrons are injected from the second electrode, and the injected electrons move via the electron transport layer to be injected into the emission layer. By recombining the holes and electrons injected into the emission layer, excitons are generated in the emission layer. The organic electroluminescence device emits light by radiation deactivation of the excitons.

SUMMARY

Embodiments are directed to a polycyclic compound and an organic electroluminescence device including the same.

The embodiments may be realized by providing a polycyclic compound represented by the following Formula 1:

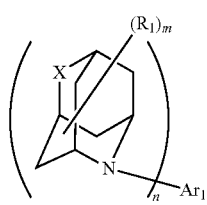

[Formula 1]

wherein, in Formula 1, X is $CR_2R_3$ or $NAr_2$, $Ar_1$ and $Ar_2$ are each independently a substituted or unsubstituted alkyl group having 1 to 50 carbon atoms, a substituted or unsubstituted aryl group having 6 to 50 ring carbon atoms, or a substituted or unsubstituted heteroaryl group having 2 to 50 ring carbon atoms. $R_1$ to $R_3$ are each independently a hydrogen atom, a deuterium atom, a halogen atom, a cyano group, a substituted or unsubstituted silyl group, a substituted or unsubstituted alkyl group having 1 to 10 carbon atoms, a substituted or unsubstituted alkoxy group having 1 to 10 carbon atoms, a substituted or unsubstituted arylthio group having 6 to 10 carbon atoms, a substituted or unsubstituted alkylamino group having 1 to 10 carbon atoms, a substituted or unsubstituted arylamino group having 6 to 20 carbon atoms, a substituted or unsubstituted aryl group having 6 to 50 ring carbon atoms, or a substituted or unsubstituted heteroaryl group having 2 to 50 ring carbon atoms, $R_1$ to $R_3$ are separate or form a ring by combining adjacent groups with each other, m is an integer of 0 to 12, and n is an integer of 1 to 3.

When X is $CR_2R_3$, n may be an integer of 1 to 3.

When X is $NAr_2$, n may be 1.

The compound represented by Formula 1 may be represented by one of the following Formulae 1-1 to 1-4:

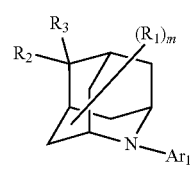

[Formula 1-1]

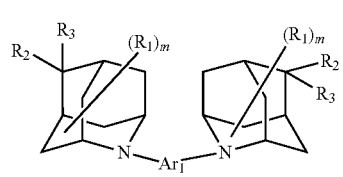

[Formula 1-2]

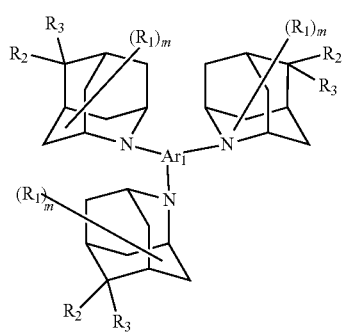

[Formula 1-3]

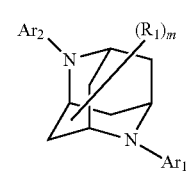

[Formula 1-4]

wherein, in Formulae 1-1 to 1-4, $Ar_1$, $Ar_2$, $R_1$ to $R_3$, and m are defined the same as those of Formula 1.

The compound represented by Formula 1 may be represented by one of the following Formulae 1-5 to 1-7:

[Formula 1-5]

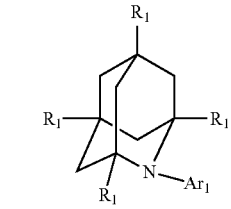

[Formula 1-6]

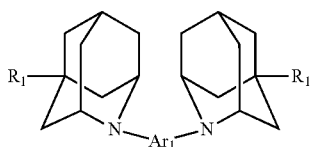

[Formula 1-7]

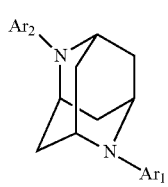

wherein, in Formulae 1-5 to 1-7, $Ar_1$, $Ar_2$, and $R_1$ are defined the same as those of Formula 1.

$Ar_1$ and $Ar_2$ may each independently be a substituted or unsubstituted phenyl group, a substituted or unsubstituted biphenyl group, a substituted or unsubstituted terphenyl group, a substituted or unsubstituted heteroaryl group including O, S or N as a heteroatom, or a substituted or unsubstituted silyl group.

When n is 1, $Ar_1$ may be a group represented by one of the following Ar-1 to Ar-8:

Ar-1

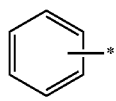

Ar-2

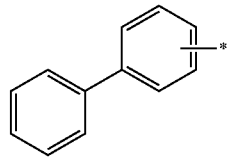

Ar-3

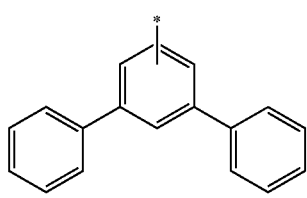

Ar-4

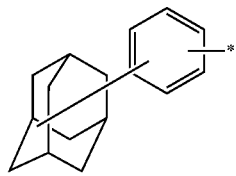

Ar-5

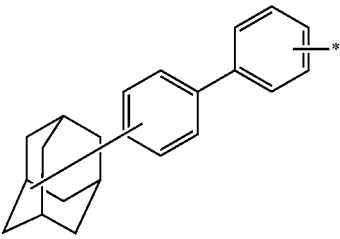

Ar-6

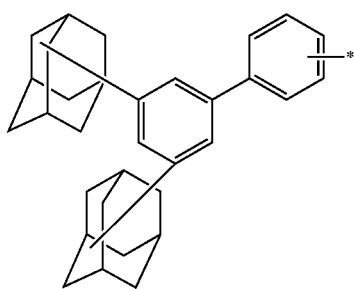

Ar-7

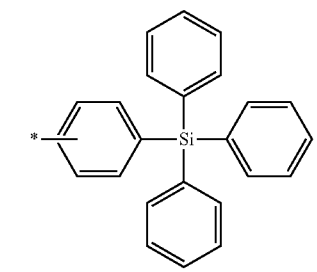

Ar-8

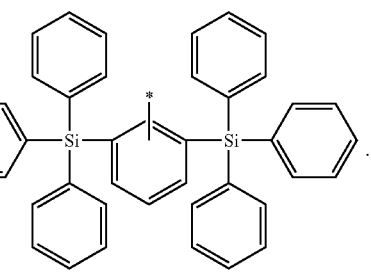

When n is 1, $Ar_1$ may be a group represented by one of the following Ar-9 to Ar-11:

Ar-9

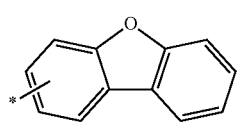

Ar-10

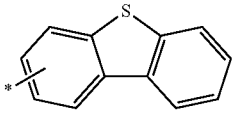

Ar-11

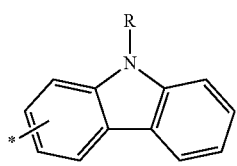

wherein, in Ar-11, R is a substituted or unsubstituted aryl group having 6 to 50 ring carbon atoms.

When n is 2, Ar$_1$ may be a group represented by one of the following Ar-12 to Ar-16:

Ar-12

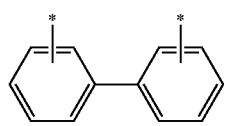

Ar-13

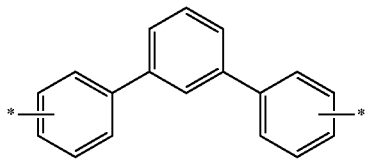

Ar-14

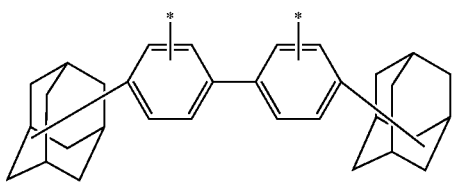

Ar-15

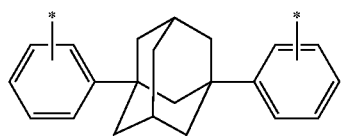

Ar-16

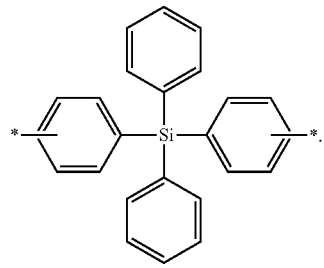

Ar$_2$ may be a substituted or unsubstituted triphenylsilyl group.

R$_1$ may be a substituted or unsubstituted phenyl group or a substituted or unsubstituted methyl group.

The compound represented by Formula 1 may be a compound of the following Compound Group 1:

[Compound Group 1]

1

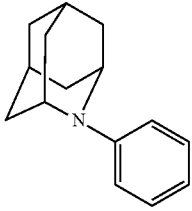

2

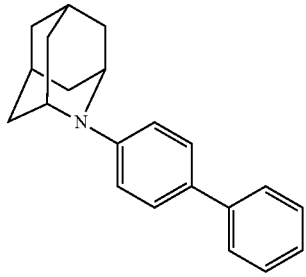

3

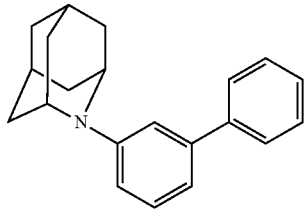

4

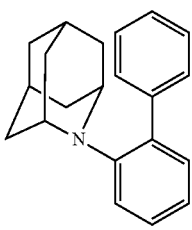

5

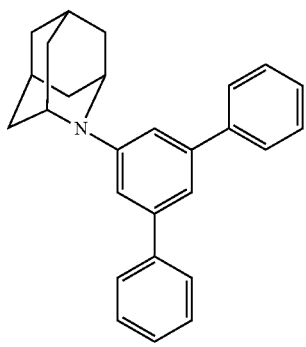

6
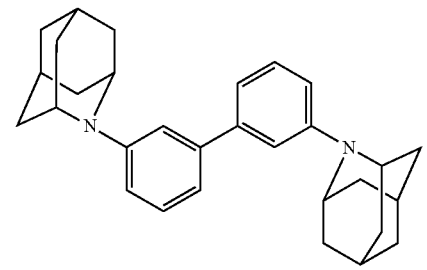
7
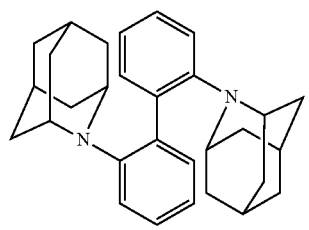
8
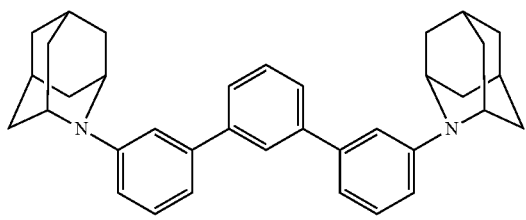
9
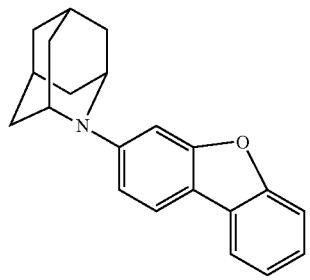
10
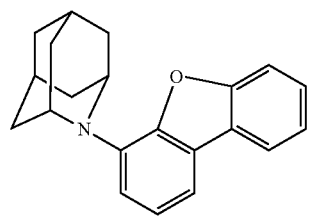
11
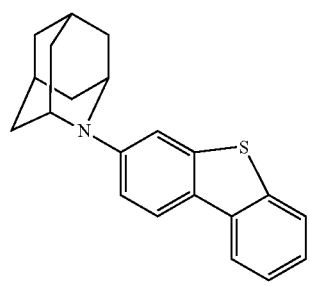
12
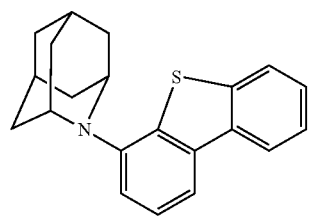
13
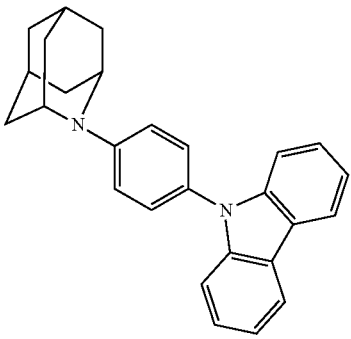
14
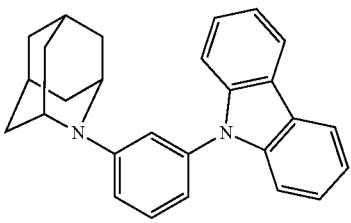
15
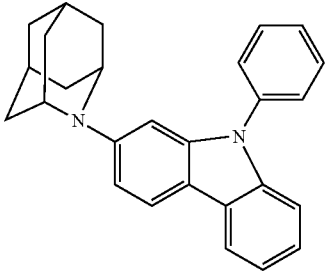
16
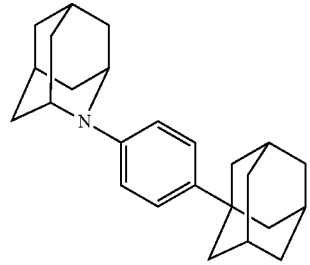
17
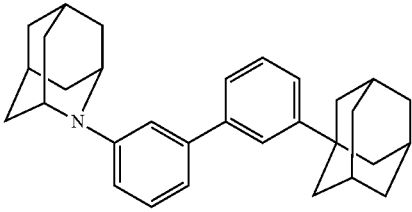

18
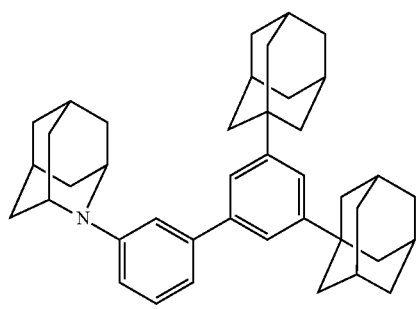
19
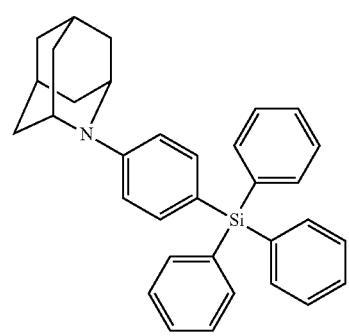
20
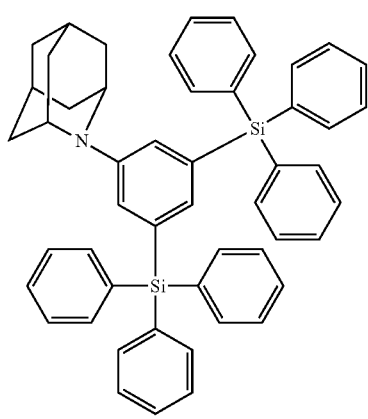
21
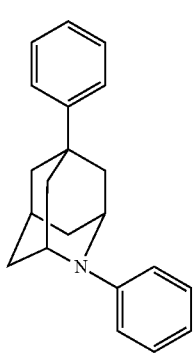
22
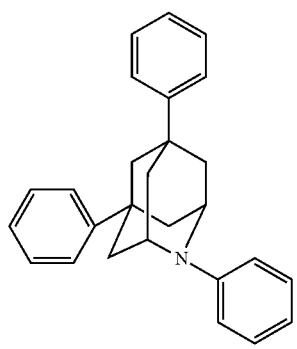
23
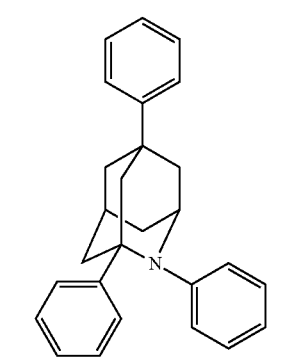
24
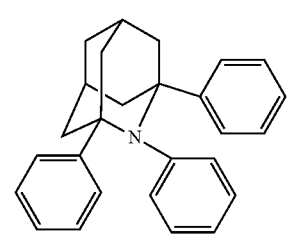
25
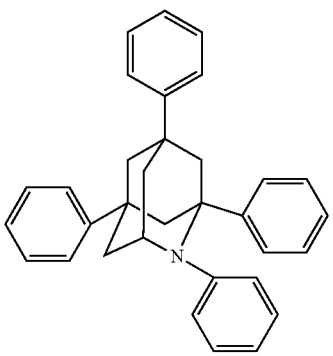
26
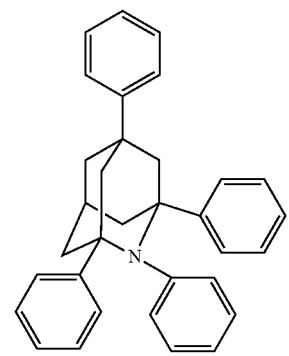

27

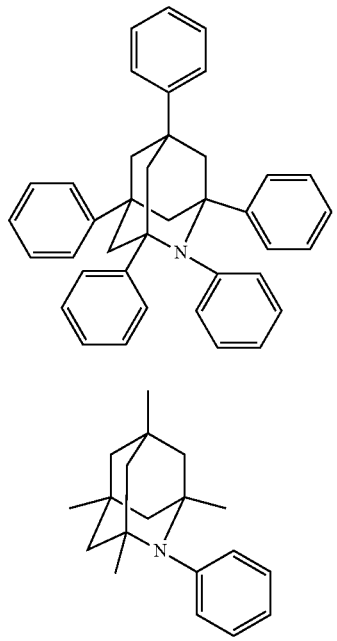

28

29

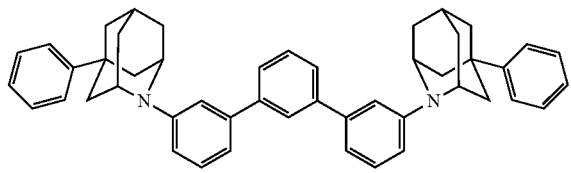

30

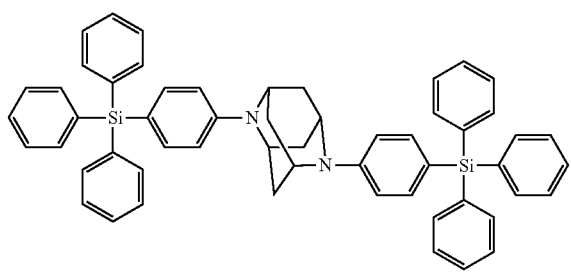

31

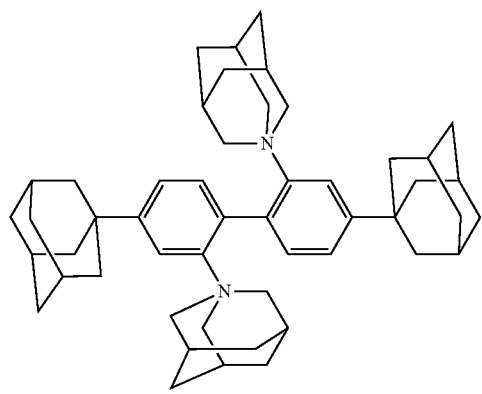

32

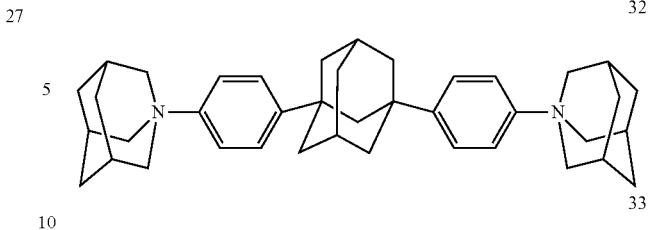

33

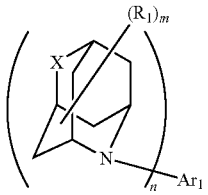

The embodiments may be realized by providing an organic electroluminescence device including a first electrode; a hole transport region on the first electrode; an emission layer on the hole transport region; an electron transport region on the emission layer; and a second electrode on the electron transport region, wherein the hole transport region includes a polycyclic compound represented by the following Formula 1:

[Formula 1]

wherein, in Formula 1, X is $CR_2R_3$ or $NAr_2$, $Ar_1$ and $Ar_2$ are each independently a substituted or unsubstituted alkyl group having 1 to 50 carbon atoms, a substituted or unsubstituted aryl group having 6 to 50 ring carbon atoms, or a substituted or unsubstituted heteroaryl group having 2 to 50 ring carbon atoms, $R_1$ to $R_3$ are each independently a hydrogen atom, a deuterium atom, a halogen atom, a cyano group, a substituted or unsubstituted silyl group, a substituted or unsubstituted alkyl group having 1 to 10 carbon atoms, a substituted or unsubstituted alkoxy group having 1 to 10 carbon atoms, a substituted or unsubstituted arylthio group having 6 to 10 carbon atoms, a substituted or unsubstituted alkylamino group having 1 to 10 carbon atoms, a substituted or unsubstituted arylamino group having 6 to 20 carbon atoms, a substituted or unsubstituted aryl group having 6 to 50 ring carbon atoms, or a substituted or unsubstituted heteroaryl group having 2 to 50 ring carbon atoms, $R_1$ to $R_3$ are separate or form a ring by combining adjacent groups with each other, m is an integer of 0 to 12, and n is an integer of 1 to 3.

The hole transport region may include a hole injection layer; and a hole transport layer between the hole injection layer and the emission layer, and the hole transport layer may include the polycyclic compound represented by Formula 1.

The emission layer may emit blue light.

The compound represented by Formula 1 may be represented by one of the following Formulae 1-1 to 1-4:

[Formula 1-1]
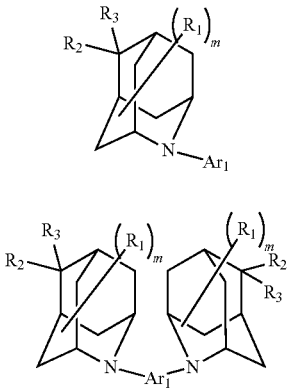

[Formula 1-2]
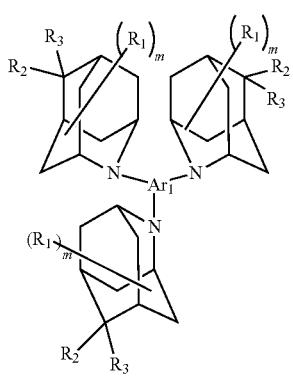

[Formula 1-3]
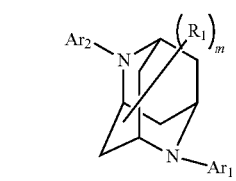
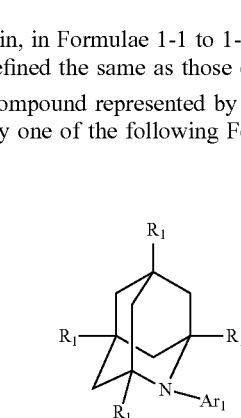

[Formual 1-4]
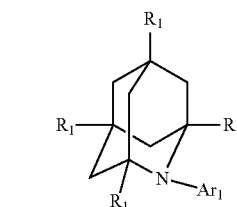
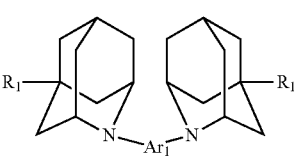

wherein, in Formulae 1-1 to 1-4, $Ar_1$, $Ar_2$, $R_1$ to $R_3$, and m are defined the same as those of Formula 1.

The compound represented by Formula 1 may be represented by one of the following Formulae 1-5 to 1-7:

[Formula 1-5]
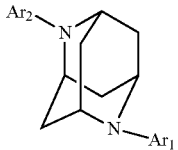

[Formula 1-6]

[Formula 1-7]

wherein, in Formulae 1-5 to 1-7, $Ar_1$, $Ar_2$, and $R_1$ are defined the same as those of Formula 1.

n may be 1, and $Ar_1$ may be a group represented by one of the following Ar-1 to Ar-11:

Ar-1
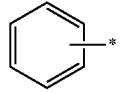

Ar-2
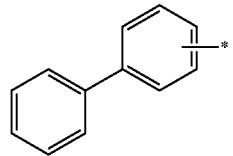

Ar-3
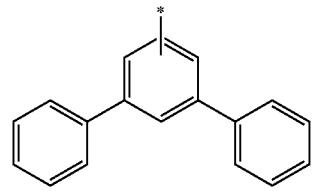

Ar-4
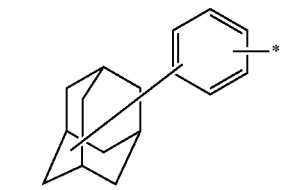

Ar-5
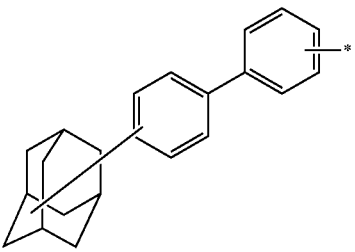

Ar-6
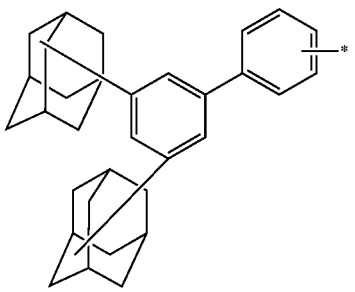

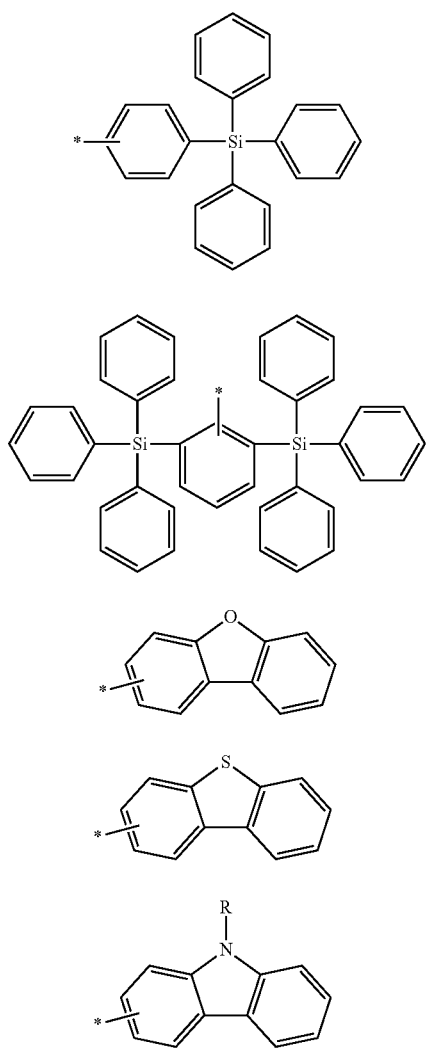

Ar-7

Ar-7

Ar-9

Ar-10

Ar-11 wherein, in Ar-11, R is a substituted or unsubstituted aryl group having 6 to 50 ring carbon atoms.

n may be 2, and $Ar_1$ may be a group represented by one of the following Ar-12 to Ar-16:

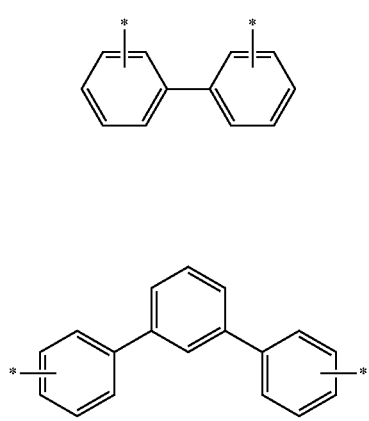

Ar-12

Ar-13

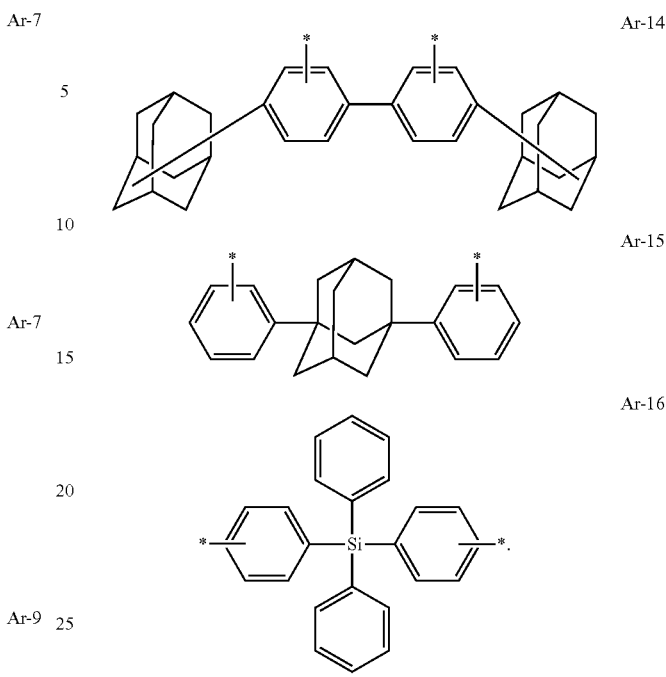

Ar-14

Ar-15

Ar-16

The hole transport region may include the compound represented by Formula 1, and the compound represented by Formula 1 may be a compound of the following Compound Group 1:

[Compound Group 1]

1

2

3

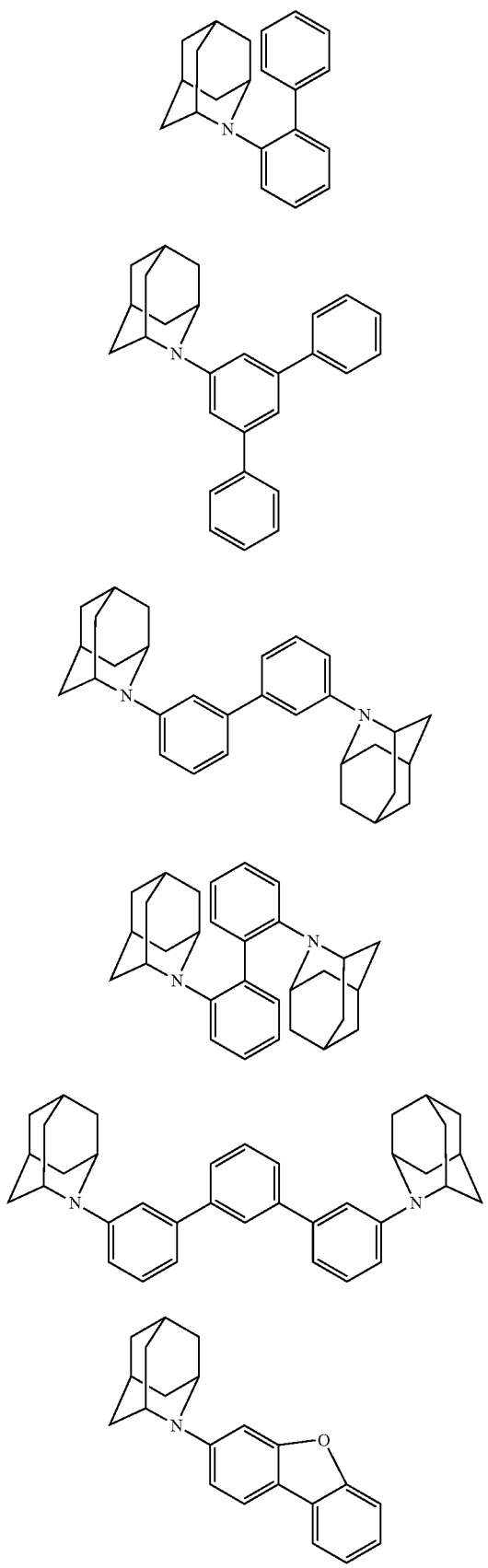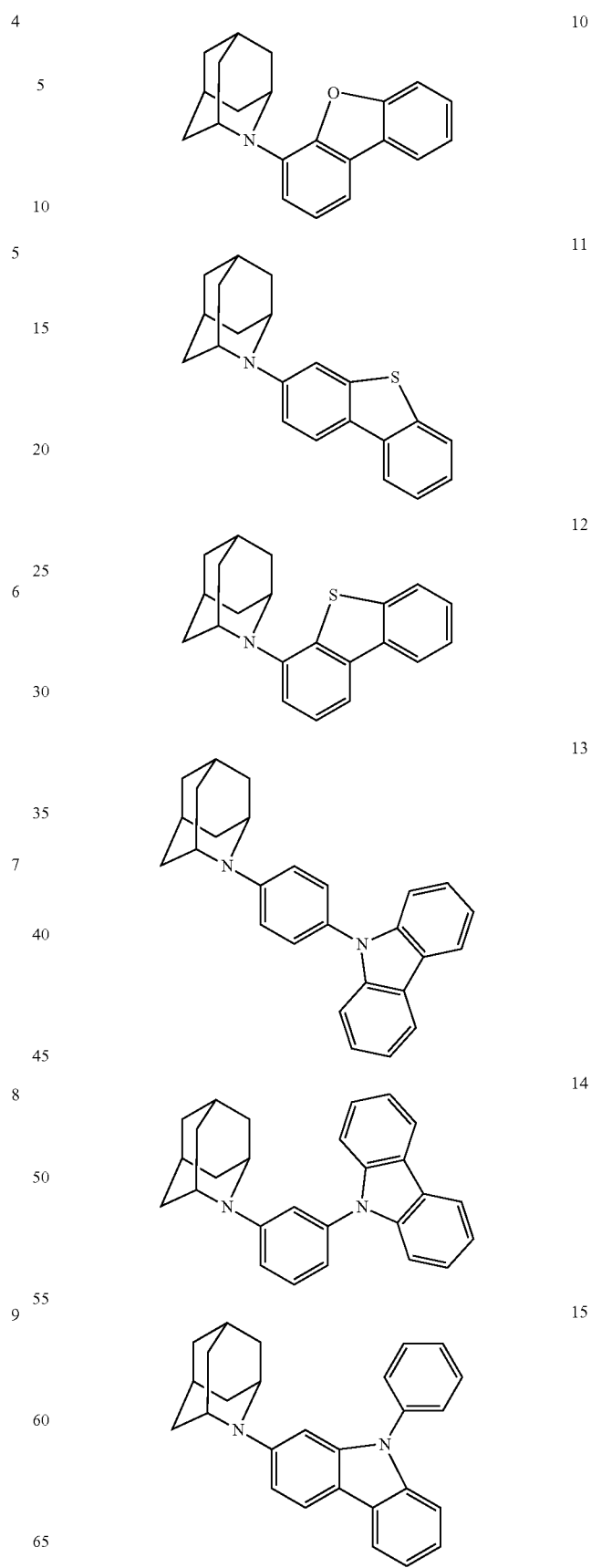

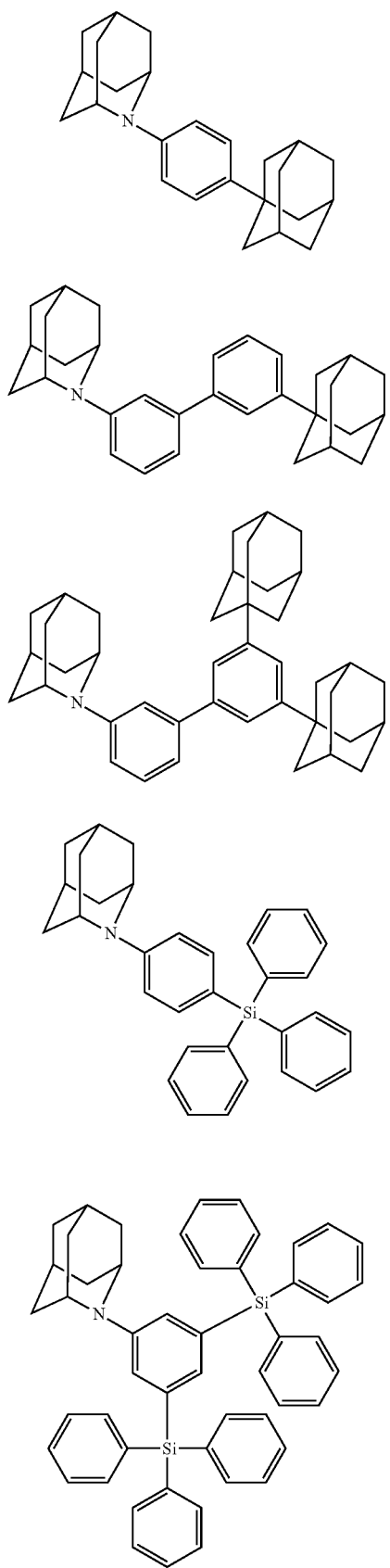
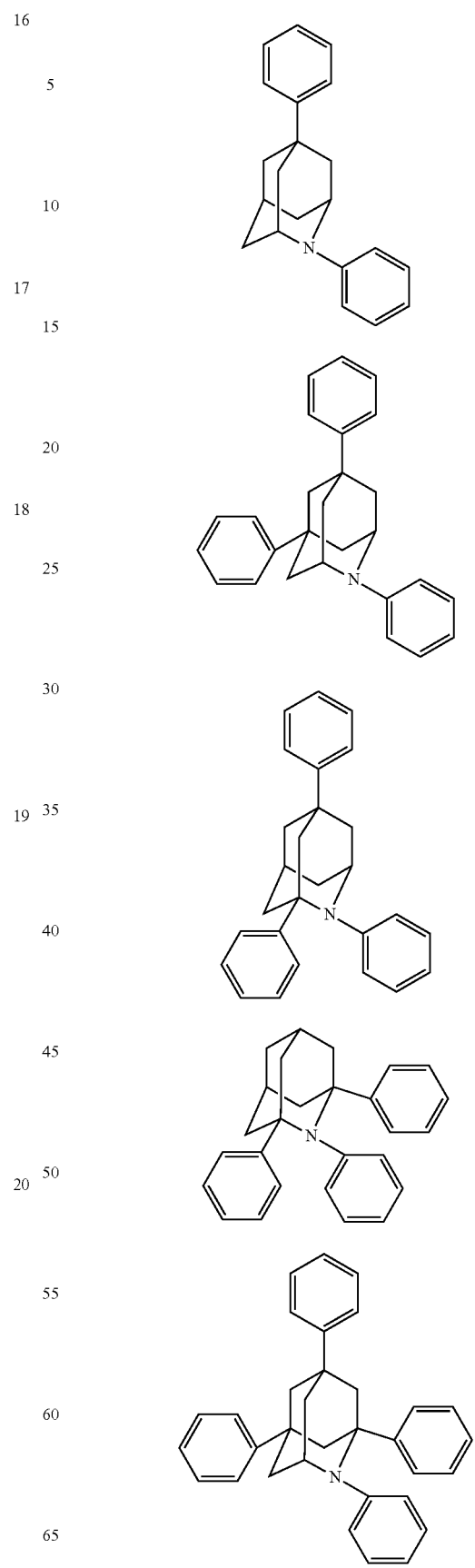

-continued

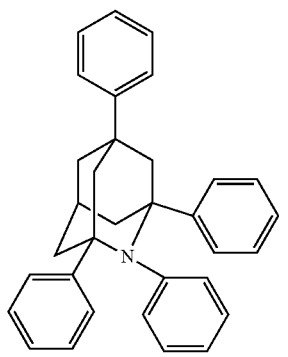
26

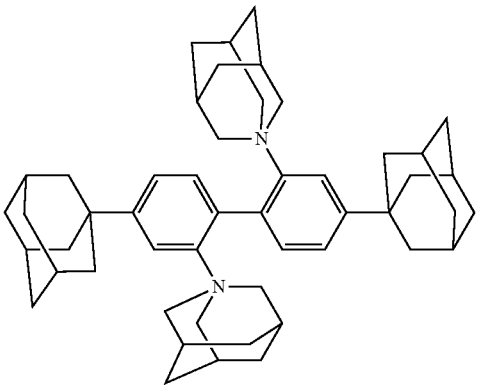
31

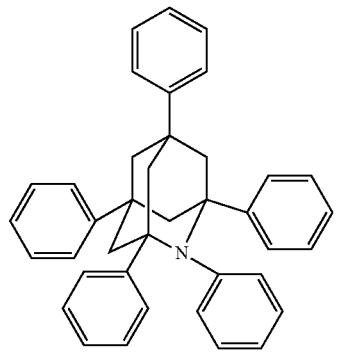
27

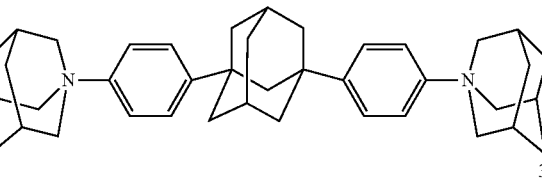
32

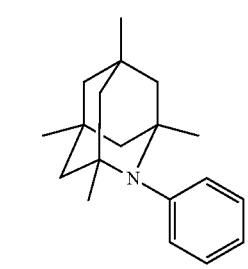
28

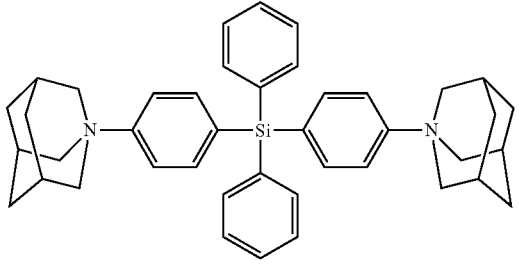
33

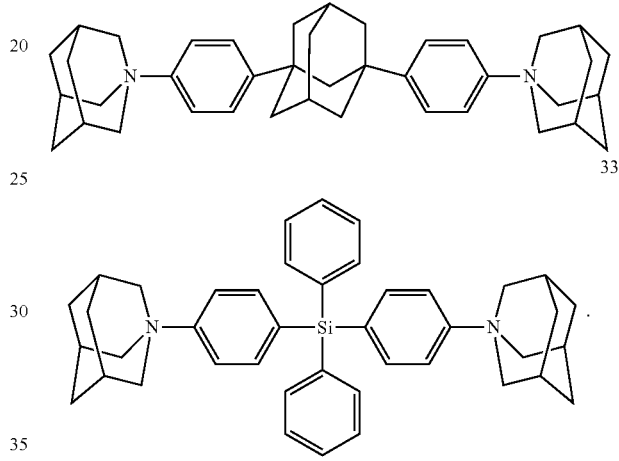

BRIEF DESCRIPTION OF THE FIGURES

Features will be apparent to those of skill in the art by describing in detail exemplary embodiments with reference to the attached drawings in which.

Figure 1:
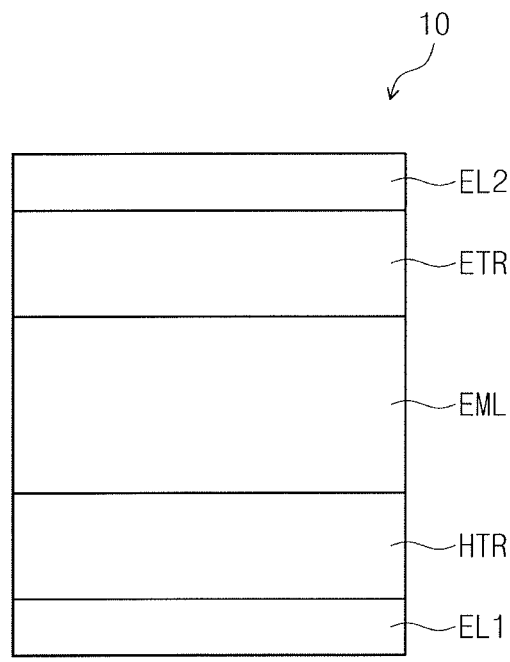
FIG. 1 illustrates a schematic cross-sectional view of an organic electroluminescence device according to an embodiment.

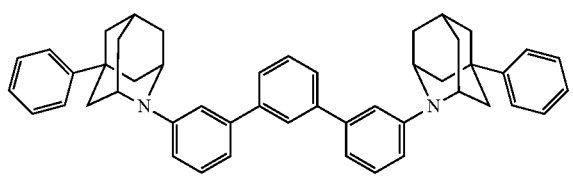
29

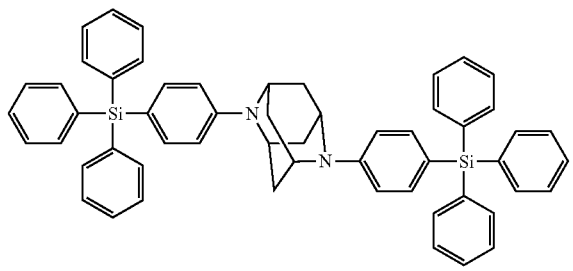
30

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

Like reference numerals refer to like elements for explaining each drawing. In the drawings, the sizes of elements may be enlarged for clarity. It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "include," "comprise" or "have," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be directly on the other part, or intervening layers may also be present. As used herein, the term "or" is not an exclusive term, e.g., the term has the same meaning as "and/or."

In the present disclosure, ——— * means a position to be connected, e.g., a bonding or linking location for another atom.

In the present disclosure, "substituted or unsubstituted" may mean unsubstituted or substituted with at least one substituent selected from the group consisting of deuterium, halogen, nitro, amino, silyl, boron, phosphine oxide, phosphine sulfide, alkyl, alkenyl, alkynyl, aryl and heterocyclic group. In addition, each of the substituent illustrated above may be substituted or unsubstituted. For example, biphenyl may be interpreted as aryl, or phenyl substituted with phenyl.

In the present disclosure, the description of forming a ring by combining adjacent groups with each other may mean forming a substituted or unsubstituted hydrocarbon ring or a substituted or unsubstituted heterocycle by combining adjacent groups with each other. The hydrocarbon ring includes an aliphatic hydrocarbon ring and an aromatic hydrocarbon ring. The heterocycle includes an aliphatic heterocycle and an aromatic heterocycle. The hydrocarbon ring and heterocycle may be a monocycle or polycycle. In addition, the ring formed by combining adjacent groups with each other may be connected with another ring to form a Spiro structure.

In the present disclosure, "an adjacent group" may mean a substituent at an atom which is directly connected with another atom at which a corresponding substituent is substituted, another substituent at an atom at which a corresponding substituent is substituted, or a substituent stereoscopically disposed at the nearest position to a corresponding substituent. For example, two methyl groups in 1,2-dimethylbenzene may be interpreted as "adjacent groups", and two ethyl groups in 1,1-diethylcyclopentene may be interpreted as "adjacent groups".

In the present disclosure, examples of a halogen atom are a fluorine atom, a chlorine atom, a bromine atom, or an iodine atom.

In the present disclosure, the alkyl group may have a linear, branched or cyclic form. The carbon number of the alkyl group may be 1 to 50, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl group means any functional group or substituent derived from an aromatic hydrocarbon ring. The aryl group may be monocyclic aryl or polycyclic aryl. The carbon number of the aryl group for forming a ring may be 6 to 50, 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylene, pyrenyl, benzofluoranthenyl, chrysenyl, etc., without limitation.

In the present disclosure, the fluorenyl group may be substituted, and two substituents may be combined with each other to form a spiro structure.

In the present disclosure, the heteroaryl group may include at least one of O, N, P, Si, or S as a heteroatom. The carbon number of the heteroaryl group for forming a ring may be 2 to 50, 2 to 30, or 2 to 20. The heteroaryl group may be monocyclic heteroaryl or polycyclic heteroaryl. Polycyclic heteroaryl may have bicyclic or tricyclic structure, for example. Examples of the heteroaryl may include thiophene, furane, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroaryl carbazole, N-alkyl carbazole, benzoxazole, benzoimidazole, benzothiazole, benzocarbazole, benzothiophene, dibenzothiophenyl, thienothiophene, benzofuranyl, phenanthroline, thiazolyl, isoxazolyl, oxadiazolyl, thiadiazolyl, benzothiazolyl, phenothiazinyl, dibenzosilole, dibenzofuranyl, etc., without limitation.

In the present disclosure, the above explanation on the aryl group may be applied to the arylene group, except that the arylene group is divalent.

In the present disclosure, the above explanation on the heteroaryl group may be applied to the heteroarylene group, except that the heteroarylene group is divalent.

In the present disclosure, the carbon number of an amino group is not specifically limited, but may be 1 to 30. The amino group may include an alkyl amino group and an aryl amino group. Examples of the amino group may include methylamino, dimethylamino, phenylamino, diphenylamino, naphthylamino, 9-methyl-anthracenylamino, triphenylamino, etc., without limitation.

Hereinafter, the polycyclic compound according to an embodiment will be explained.

The polycyclic compound according to an embodiment may be represented by the following Formula 1.

[Formula 1]

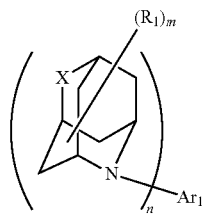

In Formula 1, X may be, e.g., $CR_2R_3$ or $NAr_2$.

$Ar_1$ and $Ar_2$ may each independently be or include, e.g., a substituted or unsubstituted alkyl group having 1 to 50 carbon atoms, a substituted or unsubstituted aryl group having 6 to 50 ring carbon atoms, or a substituted or unsubstituted heteroaryl group having 2 to 50 ring carbon atoms.

$R_1$ to $R_3$ may each independently be or include, e.g., a hydrogen atom, a deuterium atom, a halogen atom, a cyano group, a substituted or unsubstituted silyl group, a substituted or unsubstituted alkyl group having 1 to 10 carbon atoms, a substituted or unsubstituted alkoxy group having 1 to 10 carbon atoms, a substituted or unsubstituted arylthio group having 6 to 10 carbon atoms, a substituted or unsubstituted alkylamino group having 1 to 10 carbon atoms, a substituted or unsubstituted arylamino group having 6 to 20 carbon atoms, a substituted or unsubstituted aryl group having 6 to 50 ring carbon atoms, or a substituted or unsubstituted heteroaryl group having 2 to 50 ring carbon atoms. In an implementation. $R_1$ to $R_3$ may be separate or may form a ring by combining adjacent groups with each other.

m may be, e.g., an integer of 0 to 12. For example, m being 0 would have the same meaning as m being 1 and $R_1$ being hydrogen, m being 2 and both $R_1$s being hydrogen, m being 12 and all $R_1$s being hydrogen, etc. n may be, e.g., an integer of 1 to 3.

In an implementation, when X is $CR_2R_3$, n may be an integer of 1 to 3. In an implementation, when X is $NAr_2$, n may be 1.

In an implementation, the polycyclic compound represented by Formula 1 may be, e.g., represented by one of the following Formulae 1-1 to 1-4.

[Formula 1-1]

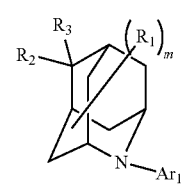

[Formula 1-2]

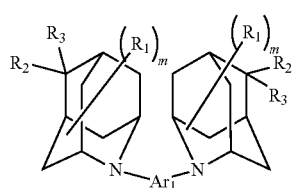

[Formula 1-3]

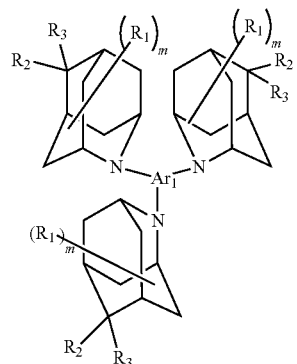

[Formual 1-4]

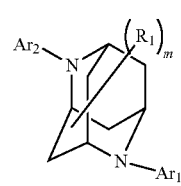

In Formulae 1-1 to 1-4, $Ar_1$, $Ar_2$, $R_1$ to $R_3$, and m may be defined the same as those of Formula 1.

For example. Formula 1-1 represents the polycyclic compound of Formula 1 in which X is $CR_2R_3$ and n is 1, Formula 1-2 represents the polycyclic compound of Formula 1 in which X is $CR_2R_3$ and n is 2, and Formula 1-3 represents the polycyclic compound of Formula 1 in which X is $CR_2R_3$ and n is 3. Formula 1-4 represents the polycyclic compound of Formula 1 in which X is $NAr_2$ and n is 1.

In an implementation, $R_2$ and $R_3$ may be hydrogen.

In an implementation, the compound represented by Formula 1 may be represented by one of the following Formulae 1-5 to 1-7.

[Formula 1-5]

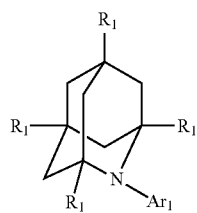

[Formula 1-6]

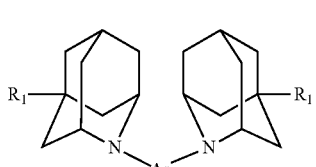

[Formula 1-7]

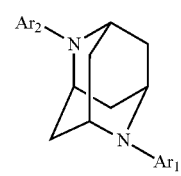

In Formulae 1-5 to 1-7, $Ar_1$, $Ar_2$, and $R_1$ may be defined the same as those of Formula 1.

In an implementation. $R_1$ may be or may include, e.g., a substituted or unsubstituted phenyl group or a substituted or unsubstituted methyl group.

In an implementation, $Ar_1$ and $Ar_2$ may each independently be or include, e.g., a substituted or unsubstituted phenyl group, a substituted or unsubstituted biphenyl group, a substituted or unsubstituted terphenyl group, a substituted or unsubstituted heteroaryl group including O, S or N as a heteroatom, or a substituted or unsubstituted silyl group.

In an implementation, in Formula 1, when n is 1, $Ar_1$ may be, e.g., a group represented by one of the following Ar-1 to Ar-8.

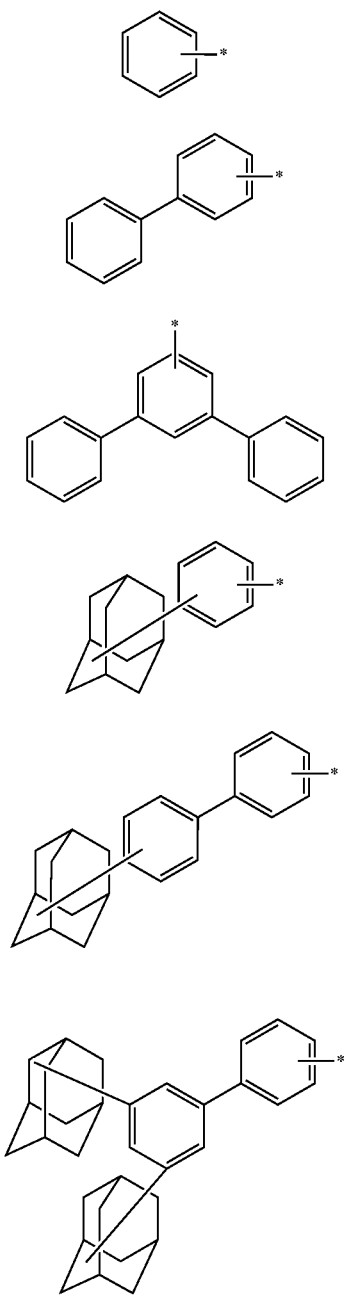

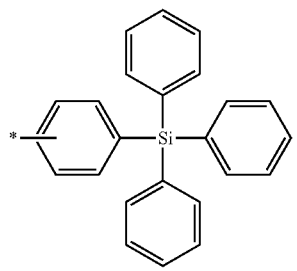

In an implementation, in Formula 1, when n is 1, $Ar_1$ may be, e.g., a group represented by one of the following Ar-9 to Ar-11.

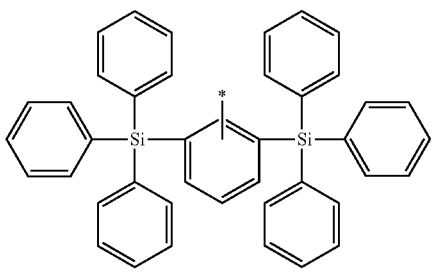

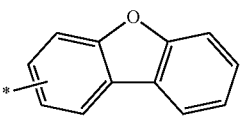

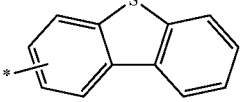

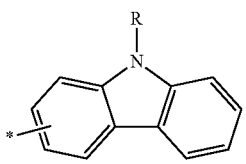

In Ar-11, R may be or may include, e.g., a substituted or unsubstituted aryl group having 6 to 50 ring carbon atoms.

In an implementation, in Formula 1, when n is 1, $Ar_1$ may be or may include, e.g., a substituted or unsubstituted phenyl group, a substituted or unsubstituted biphenyl group, a substituted or unsubstituted terphenyl group, a substituted or unsubstituted heteroaryl group including O, S or N as a heteroatom, or a substituted or unsubstituted silyl group.

In an implementation, in Formula 1, when n is 2, $Ar_1$ may be, e.g., a group represented by one of the following Ar-12 to Ar-16.

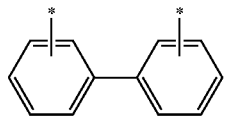

-continued

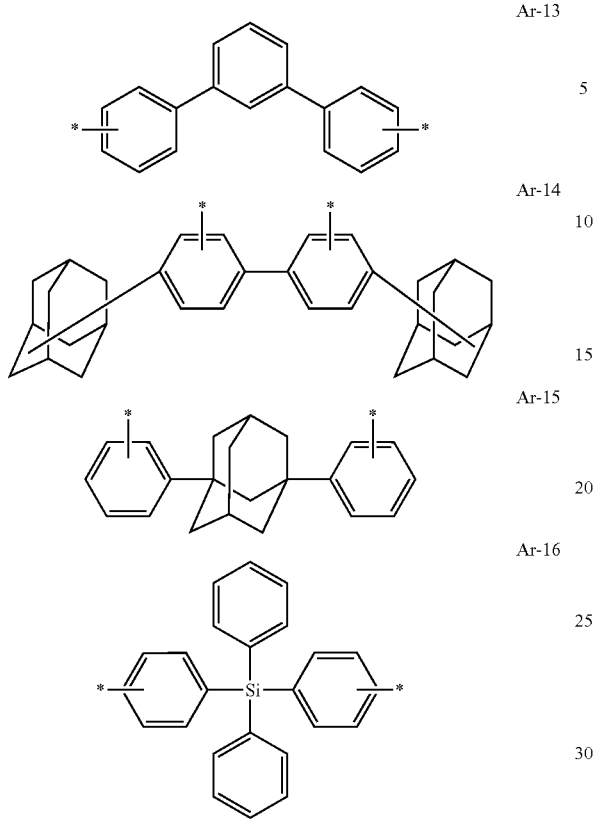

Ar-13

Ar-14

Ar-15

Ar-16

In an implementation, in Formula 1, when n is 2, $Ar_1$ may be or may include, e.g., a substituted or unsubstituted biphenyl group, a substituted or unsubstituted terphenyl group, or a substituted or unsubstituted silyl group.

In an implementation, $Ar_2$ may be or may include, e.g., a substituted or unsubstituted triphenylsilyl group.

In Formula 1, in case m is an integer of 2 or more, a plurality of $R_1$s may be the same or different from each other. For example, when m is 2, two $R_1$s may be the same or different from each other. Furthermore, when m is 3, three $R_1$s may be different from each other, two $R_1$s may be the same each other and one $R_1$ may be different, or three $R_1$s may be the same each other. For example, a plurality of substituents may be the same or different from each other.

In an implementation, $R_1$ may be or may include, e.g., a substituted or unsubstituted phenyl group or a substituted or unsubstituted methyl group.

In an implementation, the polycyclic compound represented by Formula 1 may be, e.g., a compound of the following Compound Group 1.

[Compound Group 1]

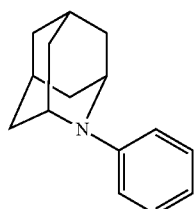

1

-continued

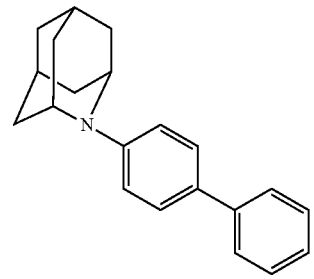

2

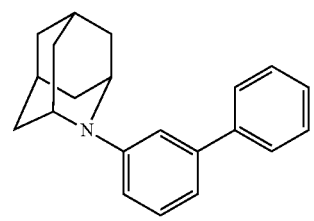

3

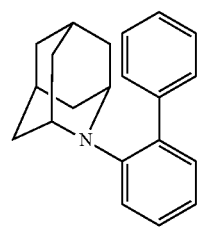

4

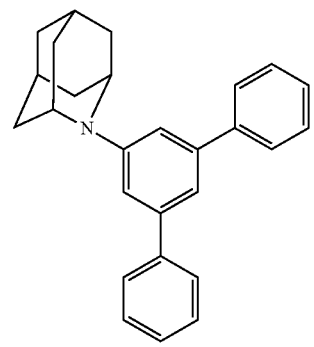

5

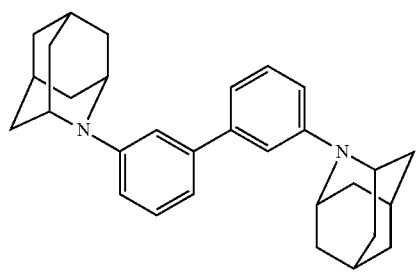

6

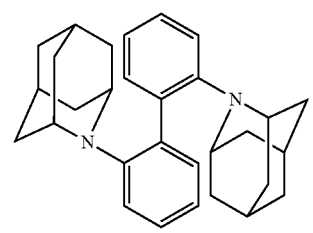

7

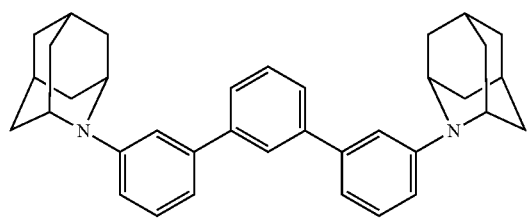
8
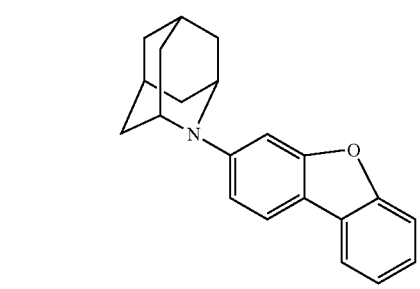
9
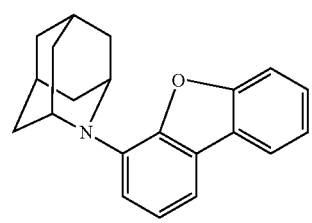
10
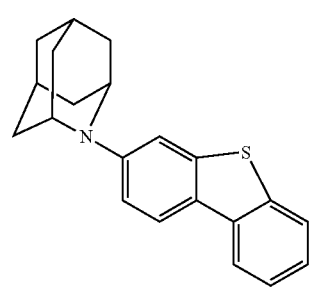
11
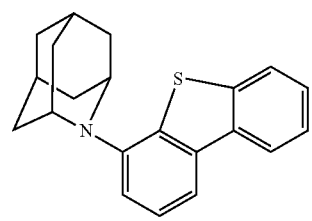
12
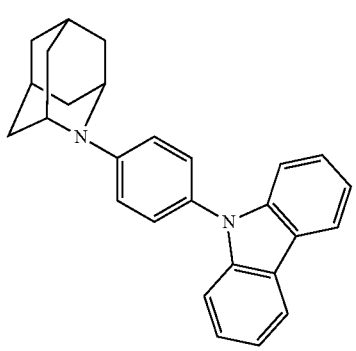
13
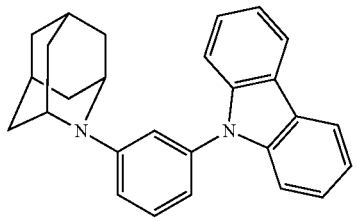
14
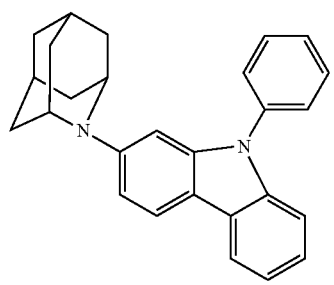
15
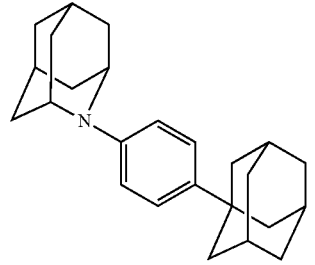
16
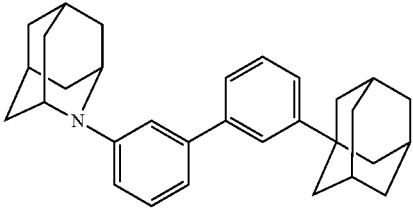
17
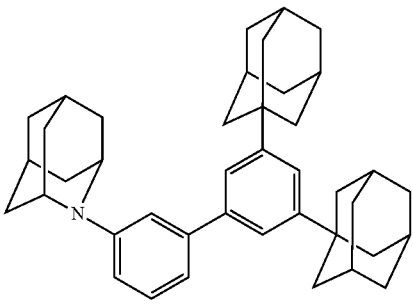
18
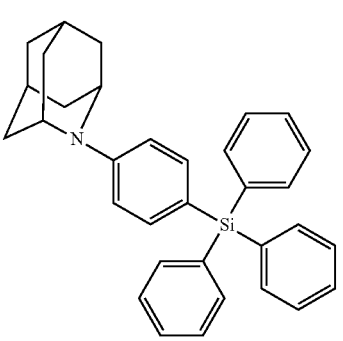
19

33
-continued
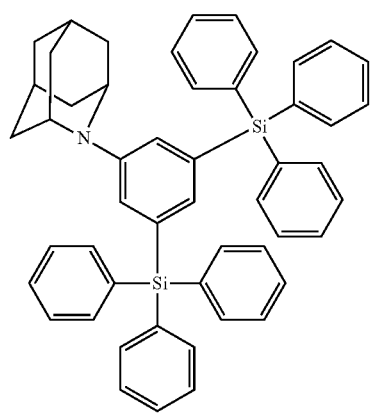
20
21
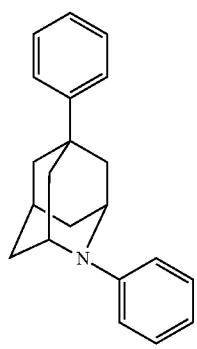
22
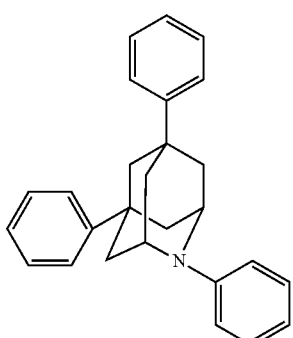
23
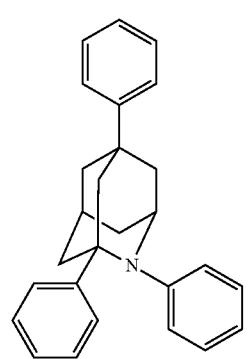
34
-continued
24
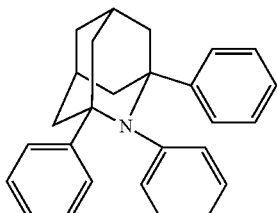
25
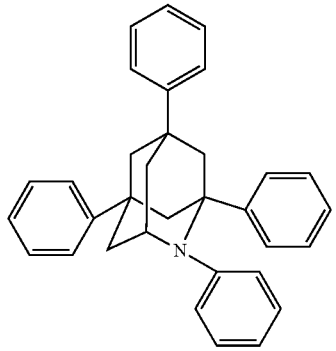
26
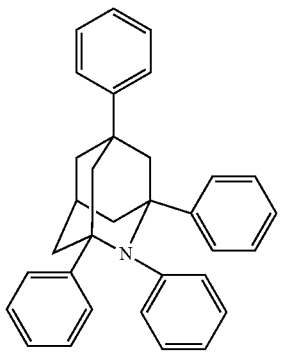
27
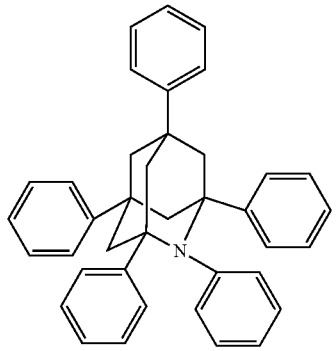
28
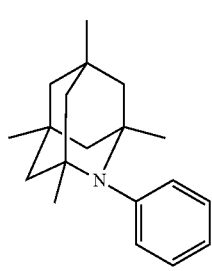

-continued

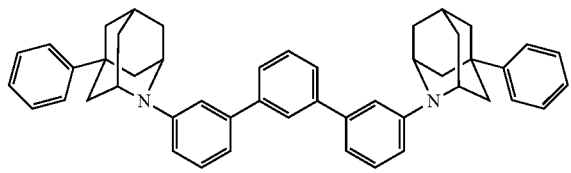
29

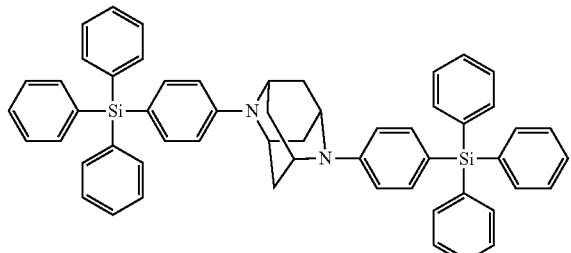
30

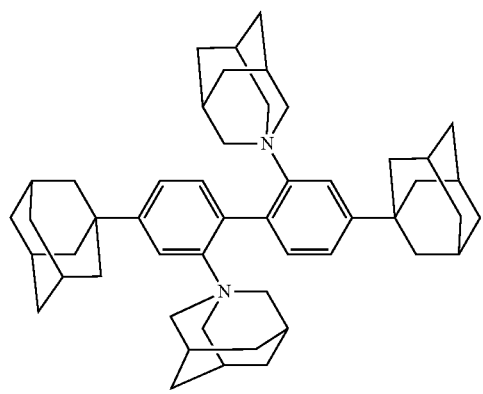
31

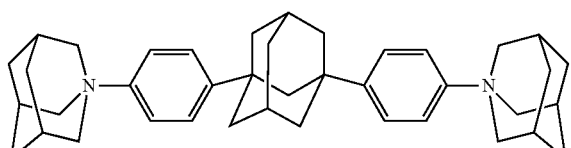
32

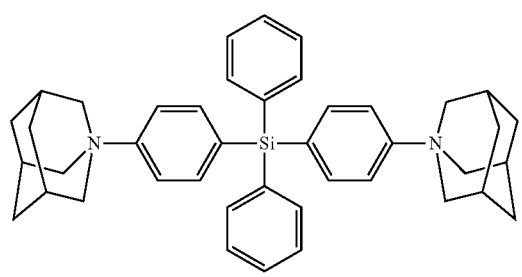
33

The above-described polycyclic compound according to an embodiment may be used as a material for an organic electroluminescence device to help improve emission efficiency of the organic electroluminescence device. The polycyclic compound according to an embodiment may have a high level of the lowest triplet excitation energy (T1). The polycyclic compound according to an embodiment may have a high level of the lowest triplet excitation energy, and the diffusion of triplet excitons generated in the emission layer into the hole transport region may be inhibited, thereby improving emission efficiency of the organic electroluminescence device.

The polycyclic compound according to an embodiment may be used as a hole transport material for an organic electroluminescence device to help improve emission efficiency and external quantum efficiency of the organic electroluminescence device.

Hereinafter, an organic electroluminescence device according to an embodiment will be explained. Repeated explanations of the above-described polycyclic compound according to an embodiment may not be given further, and unexplained parts will follow the above-description on the polycyclic compound according to an embodiment.

Figure 2:
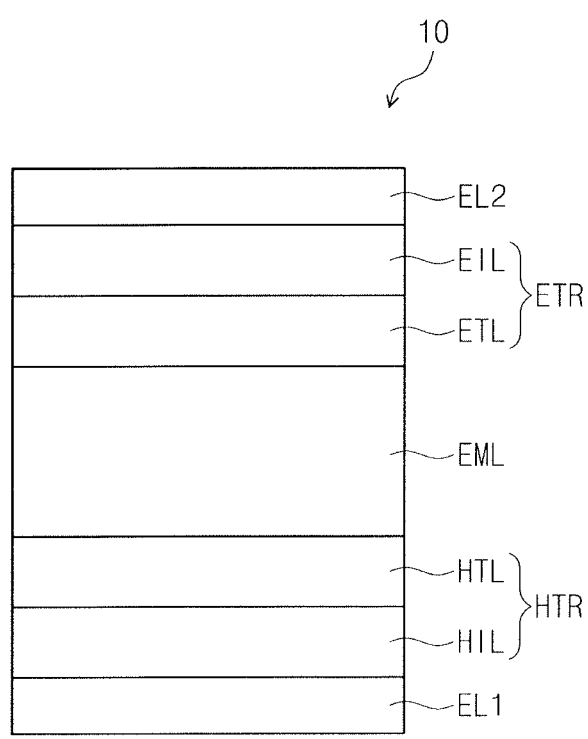
FIG. 2 illustrates a schematic cross-sectional view of an organic electroluminescence device according to an embodiment.
Figure 3:
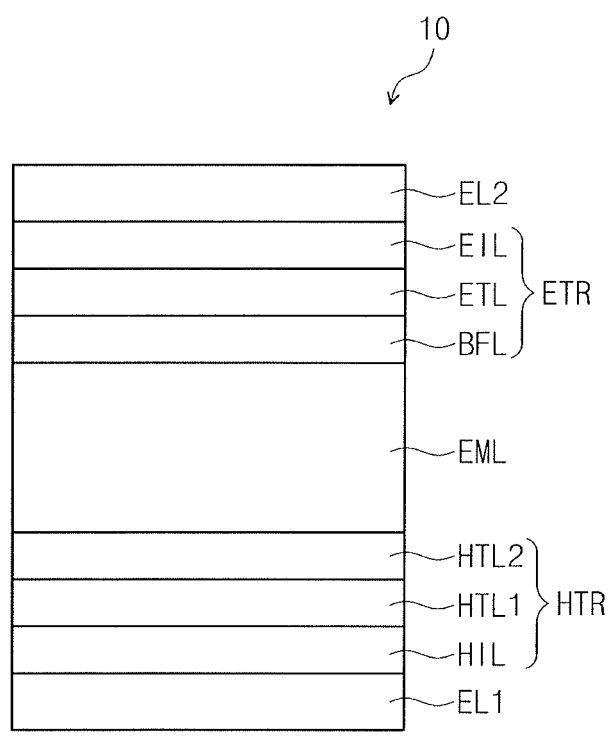
FIG. 3 illustrates a schematic cross-sectional view of an organic electroluminescence device according to an embodiment.

Each of FIGS. 1 to 3 illustrate a schematic cross-sectional view of an organic electroluminescence device according to an embodiment. Referring to FIGS. 1 to 3, an organic electroluminescence device 10 according to an embodiment may include a first electrode EL1, a hole transport region HTR, an emission layer EML, an electron transport region ETR, and a second electrode EL2, laminated in order. Comparing with FIG. 1, FIG. 2 illustrates a schematic cross-sectional view of an organic electroluminescence device according to an embodiment, in which a hole transport region HTR includes a hole injection layer HIL and a hole transport layer HTL, and an electron transport layer ETR includes an electron injection layer EIL and an electron transport layer ETL. Furthermore, FIG. 3 illustrates a schematic cross-sectional view of an organic electroluminescence device according to an embodiment, in which a hole transport region HTR includes a hole injection layer HIL, a first hole transport layer HTL1 and a second hole transport layer HTL2, and an electron transport layer ETR includes a buffer layer BFL, an electron injection layer EIL and an electron transport layer ETL.

The first electrode EL1 and the second electrode EL2 are disposed oppositely, and a plurality of organic layers may be disposed between the first electrode EL1 and the second electrode EL2. The plurality of organic layers may include a hole transport region HTR, an emission layer EML and an electron transport region ETR.

In an implementation, the organic electroluminescence device 10 according to an embodiment may include the polycyclic compound in a hole transport region HTR.

The first electrode EL1 has conductivity. The first electrode EL1 may be formed by a metal alloy or a conductive compound. The first electrode EL1 may be an anode.

The first electrode EL1 may be a transmissive electrode, a transflective electrode, or a reflective electrode. In case the first electrode EL1 is the transmissive electrode, the first electrode EL1 may be made of, e.g., a transparent metal oxide such as indium tin oxide (ITO), indium zinc oxide (IZO), zinc oxide (ZnO), indium tin zinc oxide (ITZO), etc. In case the first electrode EL1 is the transflective electrode or reflective electrode, the first electrode EL1 may include, e.g., Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may have a structure including a plurality of layers including a reflective layer or transflective layer formed using the above materials, and a transparent conductive layer formed using ITO, IZO, ZnO, ITZO, etc.

Hereinafter, a case where the above-described polycyclic compound is included in the hole transport region HTR, will be explained. In an implementation, the polycyclic compound may be included in at least one layer of one or more organic layers disposed between the first electrode EL1 and the second electrode EL2. In an implementation, the polycyclic compound may be included in the hole transport layer HIL. In an implementation, the polycyclic compound may be included in at least one layer of the first hole transport layer HTL1 or the second hole transport layer HTL2. In an implementation, the polycyclic compound may be included in both of the first hole transport layer HTL1 and the second hole transport layer HTL2, or any one of the first hole transport layer HTL1 and the second hole transport layer HTL2.

The organic electroluminescence device 10 according to an embodiment may include the above-described polycyclic compound in the hole transport region HTR. For example, the organic electroluminescence device 10 according to an embodiment may include the polycyclic compound represented by the following Formula 1 in the hole transport region HTR.

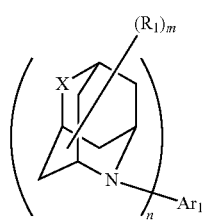

[Formula 1]

In Formula 1, X may be, e.g., $CR_2R_3$ or $NAr_2$.

$Ar_1$ and $Ar_2$ may each independently be or include, e.g., a substituted or unsubstituted alkyl group having 1 to 50 carbon atoms, a substituted or unsubstituted aryl group having 6 to 50 ring carbon atoms, or a substituted or unsubstituted heteroaryl group having 2 to 50 ring carbon atoms.

$R_1$ to $R_3$ may each independently be or include, e.g., a hydrogen atom, a deuterium atom, a halogen atom, a cyano group, a substituted or unsubstituted silyl group, a substituted or unsubstituted alkyl group having 1 to 10 carbon atoms, a substituted or unsubstituted alkoxy group having 1 to 10 carbon atoms, a substituted or unsubstituted arylthio group having 6 to 10 carbon atoms, a substituted or unsubstituted alkylamino group having 1 to 10 carbon atoms, a substituted or unsubstituted arylamino group having 6 to 20 carbon atoms, a substituted or unsubstituted aryl group having 6 to 50 ring carbon atoms, or a substituted or unsubstituted heteroaryl group having 2 to 50 ring carbon atoms. In an implementation, $R_1$ to $R_3$ may be separate or may form a ring by combining adjacent groups with each other.

m may be, e.g., an integer of 0 to 12, n may be, e.g., an integer of 1 to 3.

In Formula 1, particular explanation on the polycyclic compound according to an embodiment as described above may be applied to X, $Ar_1$, $Ar_2$, $R_1$, $R_2$, m, and n.

The polycyclic compound represented by Formula 1 may have a high level of the lowest triplet excitation energy (T1). For example, the polycyclic compound represented by Formula 1 may have the lowest triplet excitation energy of about 3.2 eV or higher.

The hole transport region HTR may be disposed on the first electrode EL1. The hole transport region HTR may include at least one of a hole injection layer HIL, a hole transport layer HTL, a hole buffer layer, or an electron blocking layer EBL. The thickness of the hole transport region HTR may be, for example, from about 1.000 Å to about 1,500 Å.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of a hole injection layer HIL or a hole transport layer HTL, or may have a single layer structure formed using a hole injection material and a hole transport material. In an implementation, the hole transport region HTR may have, e.g., a single layer structure formed using a plurality of different materials, or a laminated structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, laminated in order from the first electrode EL1.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole transport region HTR may include the above-described polycyclic compound according to an embodiment. The hole transport region HTR may include the above-described polycyclic compound according to an embodiment as a hole transport material.

The layer including the above-described polycyclic compound may be a layer adjacent to the emission layer EML. As shown in FIG. 2, when the hole transport layer HTL in the hole transport region HTR is adjacent to the emission layer EML, the hole transport layer HTL may include the polycyclic compound.

The hole transport layer HTL may include one or more of the polycyclic compound represented by Formula 1. The hole transport layer HTL may further include a suitable material in addition to the polycyclic compound represented by Formula 1.

In case the hole transport layer HTL includes the polycyclic compound, the hole injection layer HIL may include a suitable hole injection material. In an implementation, the hole injection material included in the hole injection layer HIL may include, e.g., triphenylamine-containing polyether ketone (TPAPEK), 4-isopropyl-4'-methyldiphenyliodiumtetrakis(pentafluorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenylphenylamino)triphenylamine (m-MTDATA), N,N'-di(1-naphthyl)-N,N'-diphenylbenzidine (NPB), 4,4',4''-tris(N,N-diphenylamino)triphenylamine (TDATA), 4,4',4''-tris{N,N'-2-naphthylphenylamino}-triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), etc.

In an implementation, in case the hole transport layer HTL does not include the polycyclic compound, and the emission layer EML includes the polycyclic compound, the hole transport layer HTL may include, e.g., 1,1-bis[(di-4-tolylamino)phenyl]cyclohexane (TAPC), carbazole derivatives such as N-phenyl carbazole and polyvinyl carbazole, N,N'-bis(3-methylphenyl)-N,N'-diphenyl-[1,1-biphenyl]-4, 4'-diamine (TPD), 4,4',4"-tris(N-carbazolyl)triphenylamine (TCTA), N,N'-di(1-naphthyl)-N,N'-diphenylbenzidine (NPB), etc.

The thickness of the hole transport region HTR may be from about 100 Å to about 10,000 Å, e.g., from about 100 Å to about 1,000 Å. In an implementation, in case the hole transport region HTR includes both of the hole injection layer HIL and the hole transport layer HTL, the thickness of the hole injection layer HIL may be from about 100 Å to about 10,000 Å, e.g., from about 100 Å to about 1,000 Å, and the thickness of the hole transport layer HTL may be from about 30 Å to about 1,000 Å. When the thicknesses of the hole transport region HTR, the hole injection layer HIL and the hole transport layer HTL satisfy the above-described ranges, satisfactory hole transport properties may be obtained without the substantial increase of a driving voltage.

The hole transport region HTR may further include a charge generating material in addition to the above-described materials to improve conductivity. The charge generating material may be dispersed in the hole transport region HTR uniformly or non-uniformly. The charge generating material may be, e.g., a p-dopant. In an implementation, the p-dopant may include, e.g., one of quinone derivatives, metal oxides, or cyano group-containing compounds. In an implementation, the p-dopant may include, e.g., quinone derivatives such as tetracyanoquinodimethane (TCNQ) and 2,3,5,6-tetrafluoro-tetracyanoquinodimethane (F4-TCNQ), metal oxides such as tungsten oxide and molybdenum oxide.

The hole transport region HTR may further include at least one of the hole buffer layer or the electron blocking layer EBL in addition to the hole injection layer HIL and the hole transport layer HTL, as described above. The hole buffer layer may compensate an optical resonance distance according to the wavelength of light emitted from the emission layer EML and increase light emission efficiency. Materials included in the hole transport region HTR may be used as materials included in the hole buffer layer. The electron blocking layer EBL is a layer preventing electron injection from the electron transport region ETR into the hole transport region HTR.

For In an implementation, the hole transport region HTR may include the hole injection layer HIL, the hole transport layer HTL and the electron blocking layer EBL. In an implementation, the polycyclic compound represented by Formula 1 may be included in the hole transport layer HTL.

The hole transport region HTR of the organic electroluminescence device 10 according to an embodiment may include one or more of the polycyclic compound represented by Formula 1. In an implementation, the organic electroluminescence device 10 may include, e.g., a compound of the following Compound Group 1 in the hole transport region HTR.

[Compound Group 1]

1

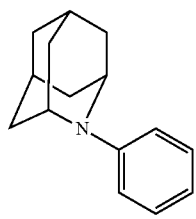

2

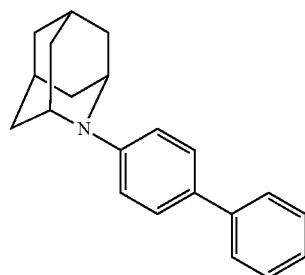

3

4

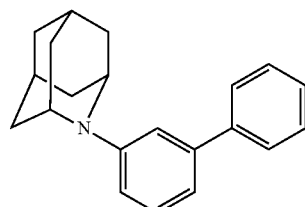

5

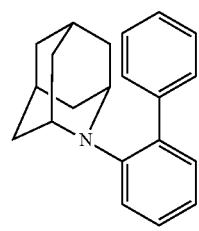

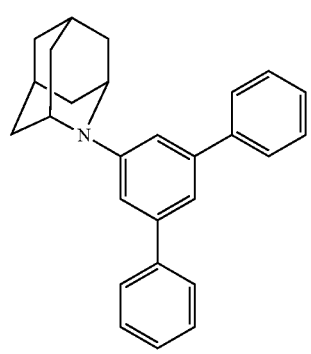

6

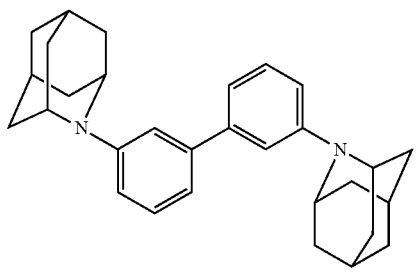

7

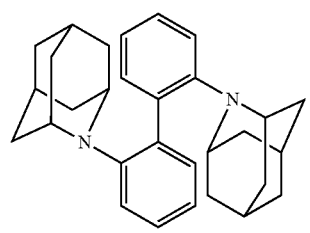

-continued
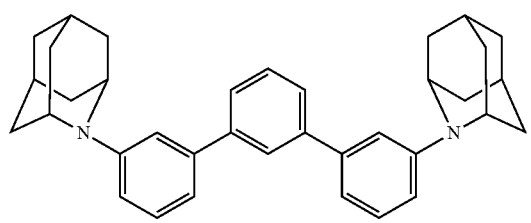
8
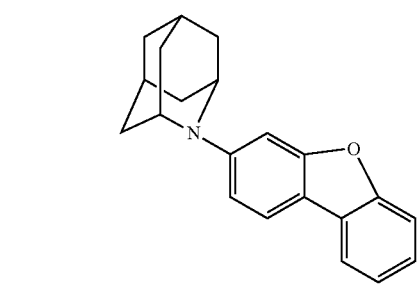
9
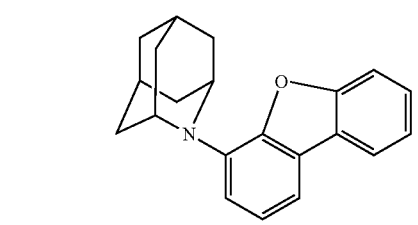
10
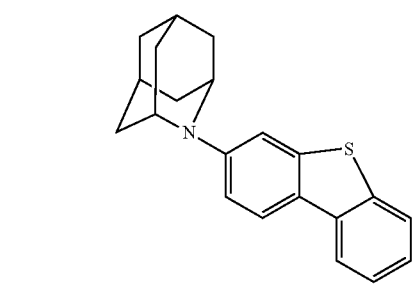
11
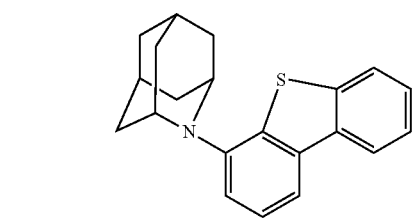
12
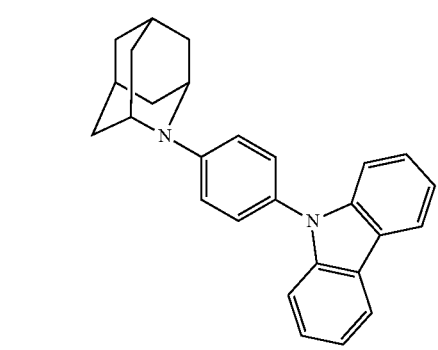
13
-continued
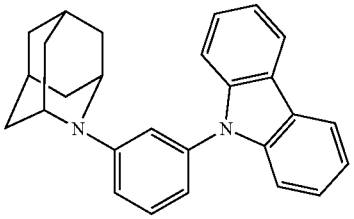
14
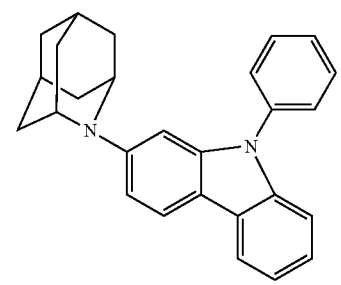
15
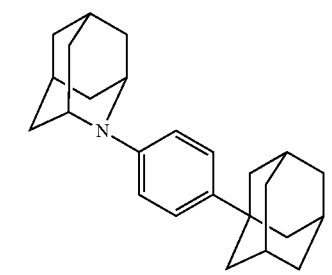
16
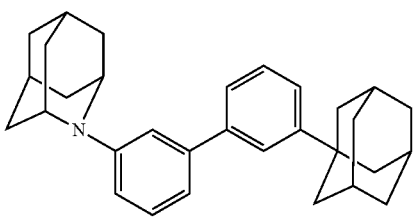
17
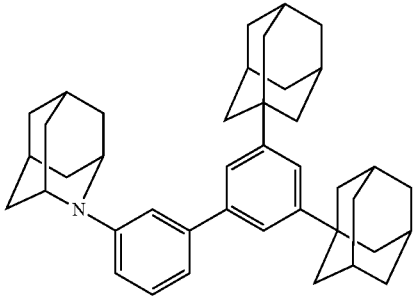
18
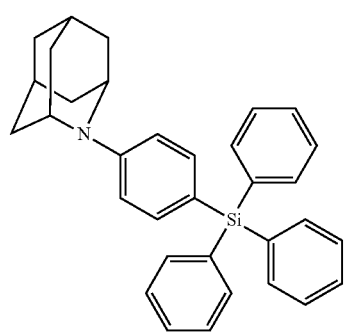
19

20
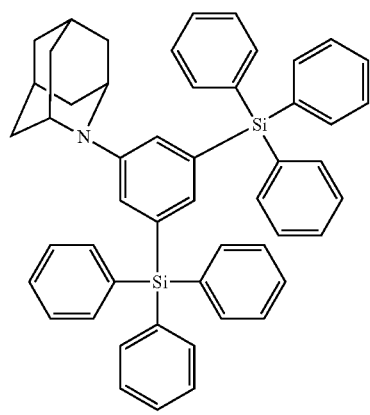
21
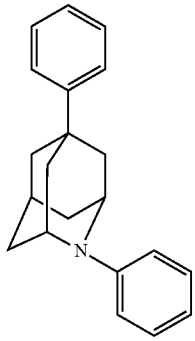
22
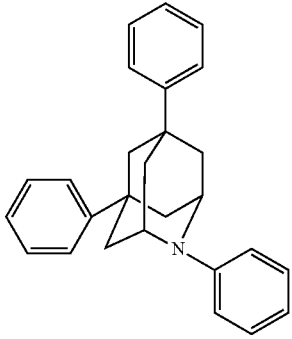
23
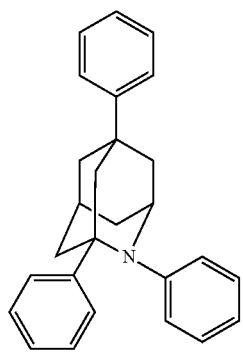
24
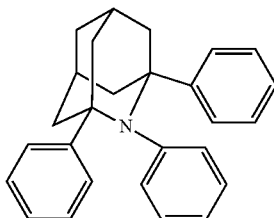
25
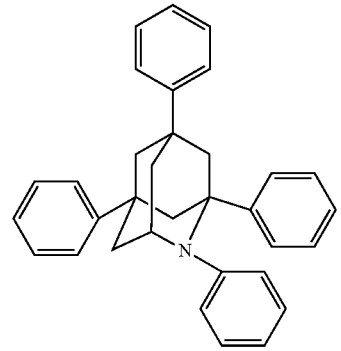
26
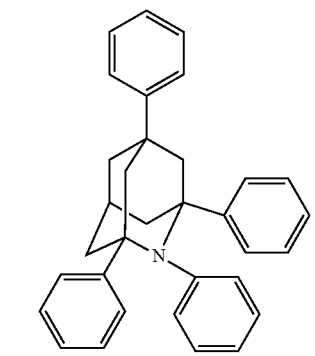
27
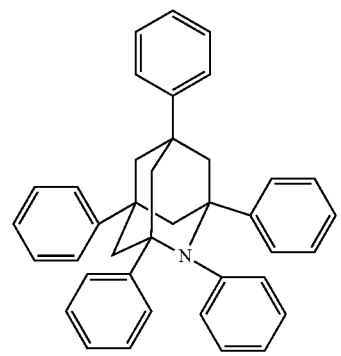
28
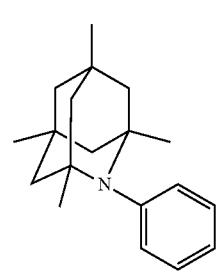

-continued

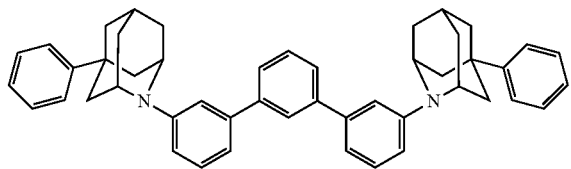
29

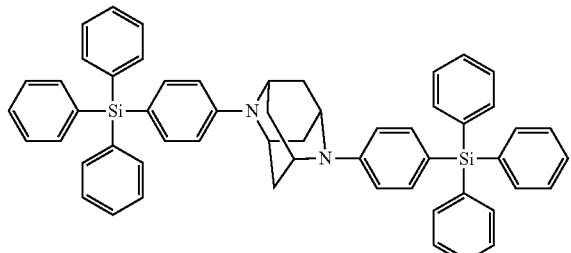
30

31

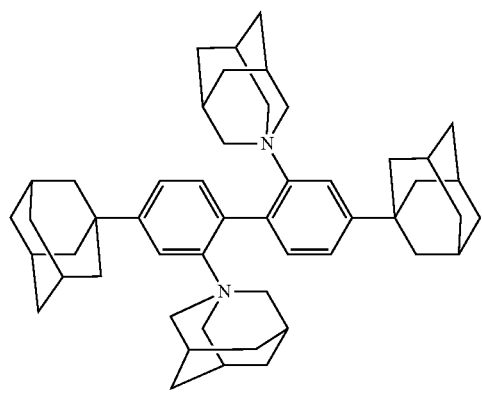
32

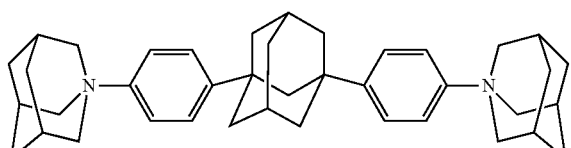
33

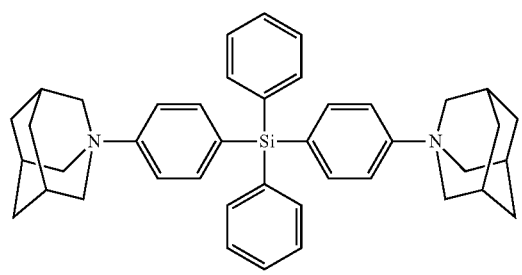

The organic electroluminescence device 10 according to an embodiment may have improved emission efficiency by including the polycyclic compounds represented by Formula 1 in the hole transport region HTR. In an implementation, the organic electroluminescence device 10 according to an embodiment may have improved external quantum efficiency by including the polycyclic compounds represented by Formula 1 in the hole transport region HTR.

The emission layer EML may be disposed on the hole transport region HTR. The thickness of the emission layer EML may be, e.g., from about 100 Å to about 600 Å. The emission layer EML may have a single layer formed using a single material, a single layer formed using a plurality of different materials, or a multilayer structure having a plurality of layers formed using a plurality of different materials.

The emission layer EML may emit one of red light, green light, blue light, white light, yellow light, or cyan light. For example, the emission layer EML of the organic electroluminescence device according to an embodiment may emit blue light.

The emission layer EML may include a fluorescent material or a phosphorescent material. In addition, the emission layer EML may include a host and a dopant.

The emission layer EML may include a host. The host may be a suitable material, e.g., tris(8-hydroxyquinolino) aluminum (Alq3), 4,4'-bis(N-carbazolyl)-1,1'-biphenyl (CBP), poly(N-vinylcarbazole) (PVK), 9,10-di(naphthalen-2-yl)anthracene (ADN), 4,4',4"-tris(carbazol-9-yl)-triphenylamine (TCTA), 1,3,5-tris(N-phenylbenzimidazol-2-yl) benzene (TPBi), 3-tert-butyl-9,10-di(naphth-2-yl) anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane (DPSiO3), octaphenylcyclotetrasiloxane (DPSiO4), 2,8-bis(diphenylphosphoryl)dibenzofuran (PPF), etc.

The dopant may include, e.g., styryl derivatives (for example, 1,4-bis[2-(3-N-ethylcarbazolyl)vinyl]benzene (BCzVB), 4-(di-p-tolylamino)-4'-[(di-p-tolylamino)styryl] stilbene (DPAVB), N-(4-((E)-2-(6-((E)-4-(diphenylamino) styryl)naphthalen-2-yl)vinyl)phenyl)-N-phenylbenzenamine (N-BDAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.

When the emission layer EML emits red light, the emission layer EML may further include, e.g., tris(dibenzoylmethanato)phenanthroline europium $(PBD:Eu(DBM)_3(Phen))$, or a fluorescent material including perylene. In case the emission layer EML emits red light, the dopant included in the emission layer EML may be selected from, e.g., a metal complex or an organometallic complex such as bis(1-phenylisoquinoline)acetylacetonate iridium (PIQIr(acac)), bis(1-phenylquinoline)acetylacetonate iridium (PQIr(acac), tris(1-phenylquinoline)iridium (PQIr), and octaethylporphyrin platinum (PtOEP), rubrene and the derivatives thereof, and 4-dicyanomethylene-2-(p-dimethylaminostyryl)-6-methyl-4H-pyran (DCM) and the derivatives thereof.

When the emission layer EML emits green light, the emission layer EML may further include a fluorescent material including, e.g., tris(8-hydroxyquinolino)aluminum $(Alq_3)$. In case the emission layer EML emits green light, the dopant included in the emission layer EML may be selected from, for example, a metal complex or an organometallic complex such as fac-tris(2-phenylpyridine)iridium $(Ir(ppy)_3)$, and coumarin and the derivatives thereof.

When the emission layer EML emits blue light, the emission layer EML may further include a fluorescent material including, e.g., spiro-DPVBi, spiro-6P, distyryl-benzene (DSB), distyryl-arylene (DSA), a polyfluorene (PFO)-based polymer, and a poly(p-phenylene vinylene) (PPV)-based polymer. In case the emission layer EML emits blue light, the dopant included in the emission layer EML may be selected from a metal complex or an organometallic complexes such as $(4,6-F_2ppy)_2Irpic$, perylene and the derivatives thereof.

The electron transport region ETR is disposed on the emission layer EML. In an implementation, the electron transport region ETR may include at least one of a hole blocking layer, an electron transport layer ETL or an electron injection layer EIL.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of the electron injection layer EIL or the electron transport layer ETL, or a single layer structure formed using an electron injection material and an electron transport material. In an implementation, the electron transport region ETR may have a single layer structure having a plurality of different materials, or a laminated structure of electron transport layer ETL/electron injection layer EIL, or hole blocking layer/electron transport layer ETL/electron injection layer EIL, laminated in order from the emission layer EML. The thickness of the electron transport region ETR may be, e.g., from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

In case the electron transport region ETR includes the electron transport layer ETL, the electron transport region ETR may include a suitable material. In an implementation, the electron transport region ETR may include, e.g., tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,08)-(1,1'-biphenyl-4-olato) aluminum (BAlq), beryylliumbis(benzoquinolin-10-olate (Bebq2), 9,10-di(naphthalen-2-yl)anthracene (ADN), or a mixture thereof.

When the electron transport region ETR includes the electron transport layer ETL, the thickness of the electron transport layer ETL may be from about 100 Å to about 1,000 Å, e.g., from about 150 Å to about 500 Å, when the thickness of the electron transport layer ETL satisfies the above-described range, satisfactory electron transport properties may be obtained without substantial increase of a driving voltage.

When the electron transport region ETR includes the electron injection layer EIL, it may include a suitable material. In an implementation, the electron transport region ETR may include, e.g., LiF, lithium quinolate (LiQ), $Li_2O$, BaO, NaCl, CsF, a lanthanide metal such as Yb, or a metal halide such as RbCl and RbI. The electron injection layer EIL also may be formed using a mixture material of an electron transport material and an insulating organo metal salt. The organo metal salt may be a material having an energy band gap of about 4 eV or more. In an implementation, the organo metal salt may include, e.g., a metal acetate, a metal benzoate, a metal acetoacetate, a metal acetylacetonate, or a metal stearate.

When the electron transport region ETR includes the electron injection layer EIL, the thickness of the electron injection layer EIL may be from about 1 Å to about 100 Å, e.g., from about 3 Å to about 90 Å. When the thickness of the electron injection layer EIL satisfies the above described range, satisfactory electron injection properties may be obtained without inducing the substantial increase of a driving voltage.

The electron transport region ETR may include a hole blocking layer, as described above. In an implementation, the hole blocking layer may include, e.g., at least one of 2,9-dimethyl-4,7-diphenyl-1,10-phenanthroline (BCP) or 4,7-diphenyl-1,10-phenanthroline (Bphen).

The second electrode EL2 is disposed on the electron transport region ETR. The second electrode EL2 has conductivity. The second electrode EL2 may be formed using a metal alloy or a conductive compound. The second electrode EL2 may be a cathode. The second electrode EL2 may be a transmissive electrode, a transflective electrode or a reflective electrode. In case the second electrode EL2 is the transmissive electrode, the second electrode EL2 may be formed using transparent metal oxides, e.g., ITO, IZO, ZnO, ITZO, etc.

When the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

In an implementation, the second electrode EL2 may be connected with an auxiliary electrode. When the second electrode EL2 is connected with the auxiliary electrode, the resistance of the second electrode EL2 may decrease.

In the organic electroluminescence device 10, according to the application of a voltage to each of the first electrode EL1 and the second electrode EL2, holes injected from the first electrode EL1 move via the hole transport region HTR to the emission layer EML, and electrons injected from the second electrode EL2 move via the electron transport region ETR to the emission layer EML. The electrons and the holes are recombined in the emission layer EML to generate excitons, and light is emitted via the transition of the excitons from an excited state to a ground state.

In case the organic electroluminescence device 10 is a top emission type, the first electrode EL1 may be a reflective electrode, and the second electrode EL2 may be a transmissive electrode or a transflective electrode. In case the organic electroluminescence device 10 is a bottom emission type, the first electrode EL1 may be a transmissive electrode or a transflective electrode, and the second electrode EL2 may be a reflective electrode.

The organic electroluminescence device according to an embodiment may include the above-described polycyclic compound, thereby securing improved emission efficiency. Furthermore, in the organic electroluminescence device according to an embodiment including the above-described polycyclic compound having a high level of the lowest triplet energy in the hole transport region, the diffusion of triplet excitons generated in the emission layer may be inhibited, thereby attaining high external quantum efficiency.

In an implementation, the organic electroluminescence device according to an embodiment may be a blue light emitting device, a green light emitting device, a red light emitting device or a white light emitting device. In an implementation, the organic electroluminescence device according to an embodiment may have high emission efficiency, when it is a blue light emitting device.

Hereinafter, the polycyclic compound according to an embodiment and the organic electroluminescence device including the same will be explained in more detail with reference to Examples and Comparative Examples.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

1. Synthesis of Polycyclic Compound

The synthetic method of the polycyclic compound according to an embodiment will be explained in more detail by illustrating the synthetic method of the compounds below.

(Synthesis of Compound 32)

[Reaction Scheme 1]

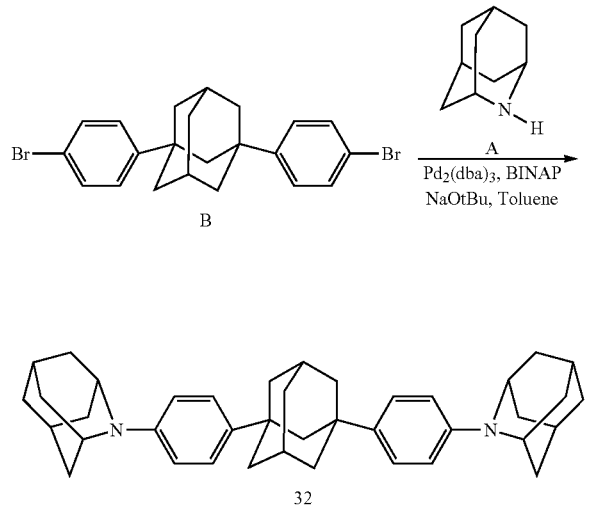

Compound 32, a polycyclic compound according to an embodiment, may be synthesized, e.g., by the reaction of aryl halide and 2-aza-adamantane as shown in the above Reaction Scheme 1.

Under an argon atmosphere, Compound A (3.00 g, 21.9 mmol), Compound B (4.88 g, 10.9 mmol), tris(dibenzilidenacetone)dipalladium (601 mg, 0.656 mmol), (±)-BINAP (1.23 g, 1.97 mmol) and sodium-tert-butoxide (10.5 g, 109 mmol) were added to toluene (200 mL) in order, and the mixture was heated to reflux at about 110° C. for about 18 hours. After cooling to ambient temperature, precipitated solid was filtered. The precipitated solid was purified by column chromatography (silica) and recrystallized with toluene/ethanol to obtain Compound 32 (8.43 g, 15.1 mmol, yield 69%). The structure of product was identified using FAB-MS (m/z=558).

(Synthesis of Compound 33)

[Reaction Scheme 2]

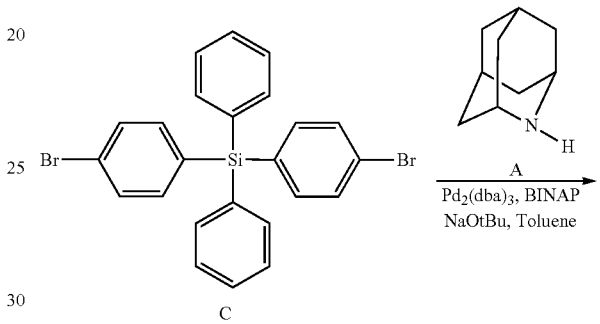

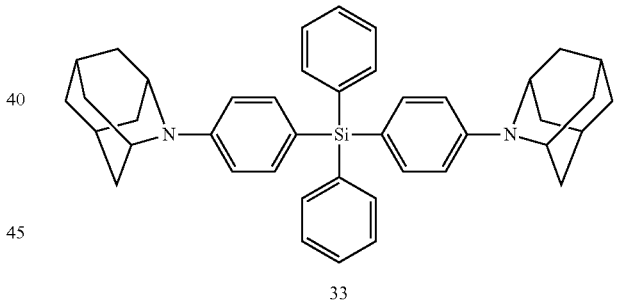

Compound 33, a polycyclic compound according to an embodiment, may be synthesized, e.g., by the reaction of aryl halide and 2-aza-adamantane as shown in the above Reaction Scheme 2.

Under an argon atmosphere, Compound A (2.50 g, 18.2 mmol), Compound C (4.50 g, 9.11 mmol), tris(dibenzilidenacetone)dipalladium (500 mg, 0.547 mmol). (±)-BINAP (1.02 g, 1.64 mmol) and sodium-tert-butoxide (8.75 g, 91.1 mmol) were added to toluene (200 mL) in order, and the mixture was heated to reflux at about 110° C. for about 18 hours. After cooling to ambient temperature, precipitated solid was filtered. The precipitated solid was purified by column chromatography (silica) and recrystallized with toluene/ethanol to obtain Compound 33 (7.96 g, 13.1 mmol, yield 72%). The structure of product was identified using FAB-MS (m/z=606).

(Synthesis of Compound 17)

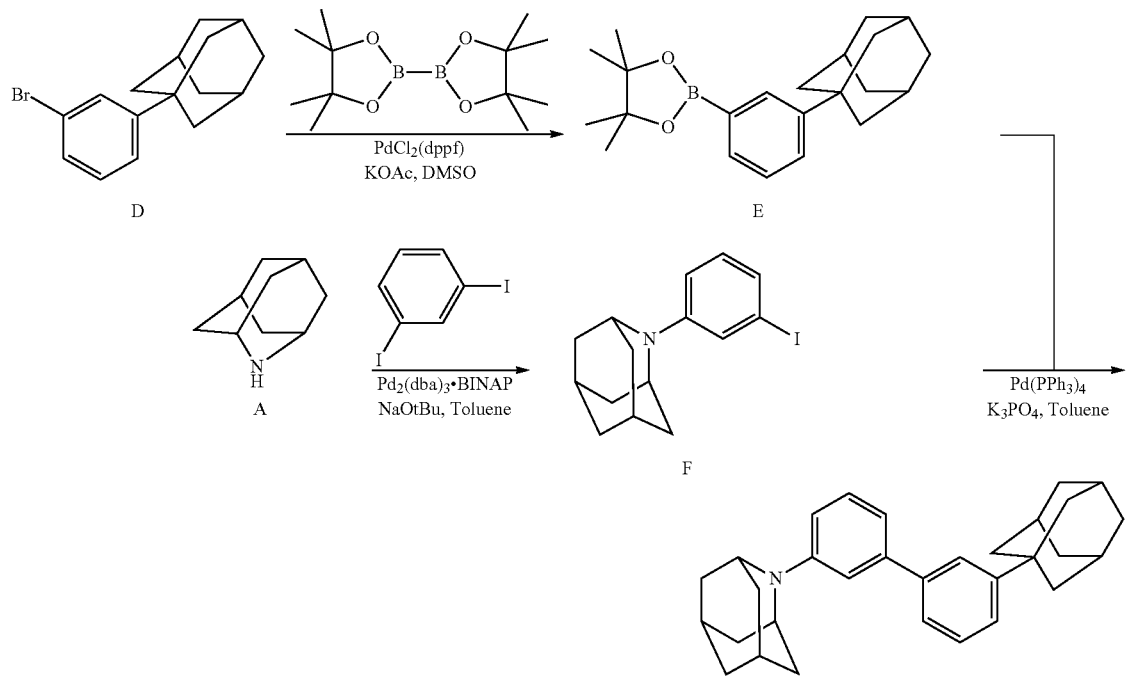

Compound 17, a polycyclic compound according to an embodiment, may be synthesized, e.g., as shown in the above Reaction Scheme 3.

Under an argon atmosphere, Compound D (7.98 g, 82.2 mmol), bis(pinacolato)diboron (13.9 g, 54.8 mmol), [1,1'-bis(diphenylphosphino)ferrocene]palladium dichloride (dichloromethane complex) (1.12 g, 1.37 mmol) and potassium acetate (8.06 g, 82.2 mmol) were added to DMSO (300 mL) in order, and the mixture was heated to reflux at about 90° C. for about 8 hours. After cooling to ambient temperature, precipitated solid was filtered. The precipitated solid was purified by column chromatography (silica) and recrystallized with toluene to obtain Compound E (6.30 g, 18.6 mmol, yield 68%).

Under an argon atmosphere, Compound A (3.06 g, 22.3 mmol), 1,3-diiodobenzene (7.37 g, 22.3 mmol), tris(dibenzilidenacetone)dipalladium (1.02 g, 1.12 mmol), BINAP (1.39 g, 2.23 mmol) and sodium-tert-butoxide (6.44 g, 67.0 mmol) were added to toluene (300 mL) in order, and the mixture was heated to reflux at about 90° C. for about 5 hours. After cooling to ambient temperature, precipitated solid was filtered. The precipitated solid was purified by column chromatography (silica) and recrystallized with toluene to obtain Compound F (5.53 g, 16.3 mmol, yield 73%).

Under an argon atmosphere, Compound E (4.86 g, 14.4 mmol), Compound F (4.88 g, 14.4 mmol), tetrakis(triphenylphosphine)palladium (831 mg, 0.719 mmol) and potassium phosphate (9.15 g, 43.1 mmol) were added to toluene (300 mL) in order, and the mixture was heated to reflux at about 90° C. for about 6 hours. After cooling to ambient temperature, precipitated solid was filtered. The precipitated solid was purified by column chromatography (silica) and recrystallized with toluene to obtain Compound 17 (4.75 g, 11.2 mmol, yield 78%). The structure of product was identified using FAB-MS (m/z=423).

2. Manufacturing of organic electroluminescence devices including polycyclic compounds and evaluation thereof.

(Manufacturing of Organic Electroluminescence Devices)

Organic electroluminescence devices were manufactured by the following method. The organic electroluminescence devices of Examples 1 to 3 were manufactured by using Compounds 32, 33 and 17 as a hole transport material. The organic electroluminescence devices of Comparative Examples 1 to 4 were manufactured by using the following Comparative Compounds C1 to C4 as a hole transport material.

Table 1 shows the compounds used in the hole transport layer for Examples 1 to 3 and Comparative Examples 1 to 4.

TABLE 1

| Compound 32 | 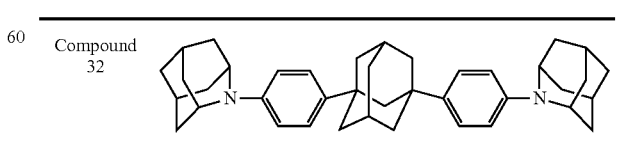 |
|---|---|
| | 32 |

TABLE 1-continued

Compound 33

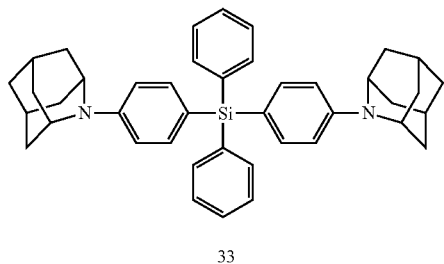

33

Compound 17

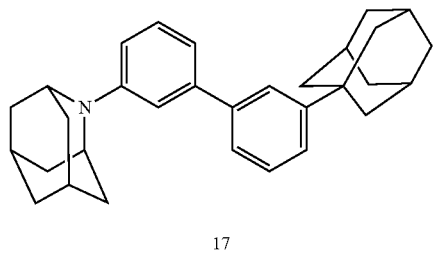

17

Comparative Compound C1

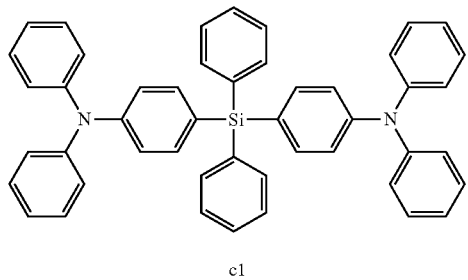

c1

Comparative Compound C2

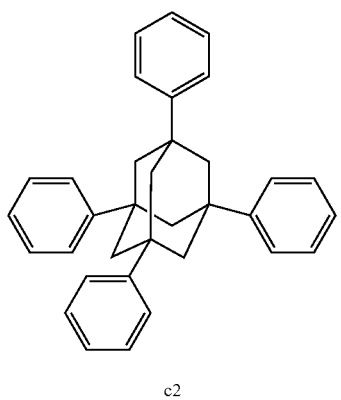

c2

Comparative Compound C3

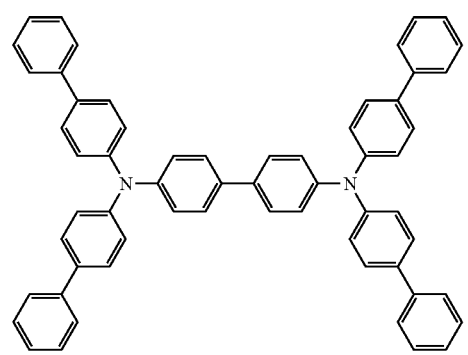

c3

TABLE 1-continued

Comparative Compound C4

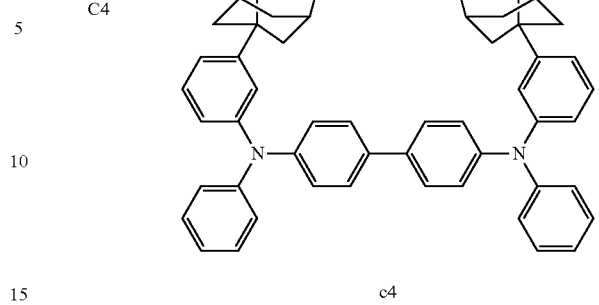

c4

Organic electroluminescence devices of the Examples and Comparative Examples were manufactured by the following method.

ITO was patterned on a glass substrate to a thickness of about 150 nm, followed by washing with ultrapure water and performing UV ozone treatment for about 10 minutes. A hole injection layer was formed using HAT-CN to a thickness of about 10 nm. After that, a first hole transport layer HTL1 was formed using α-NPD to a thickness of about 80 nm, and then a second hole transport layer HTL2 was formed using the Example Compounds or Comparative Compounds to a thickness of about 5 nm.

Next, an emission layer was formed by co-deposition of ACRSA and DPEPO in a ratio of 18:82 to a thickness of about 20 nm. After that, a buffer layer was formed using DPEPO to a thickness of about 10 nm.

An electron transport layer was formed using TPBi to a thickness of about 30 nm, and an electron injection layer was formed using LiF to a thickness of about 0.5 nm. A second electrode was formed using Al to a thickness of about 100 nm.

In the Examples and Comparative Examples, the hole injection layer, first hole transport layer, second hole transport layer, emission layer, buffer layer, electron transport layer, electron injection layer and second electrode were formed by using a vacuum deposition apparatus.

(Property Evaluation of Organic Electroluminescence Devices)

Emission efficiency at a current density of 10 mA/cm² was measured to evaluate the properties of the organic electroluminescence devices manufactured in the Examples and Comparative Examples. The voltage and current density of organic electroluminescence devices were measured by using a source meter (Keithley Instruments, 2400 series). Property evaluation results of the organic electroluminescence devices are shown in Table 2 below.

TABLE 2

| Examples | Second hole transport layer | Emission efficiency (%) |
| --- | --- | --- |
| Example 1 | Compound 32 | 112 |
| Example 2 | Compound 33 | 111 |
| Example 3 | Compound 17 | 112 |
| Comparative Example 1 | Comparative Compound C1 | 100 |
| Comparative Example 2 | Comparative Compound C2 | 83 |
| Comparative Example 3 | Comparative Compound C3 | 70 |
| Comparative Example 4 | Comparative Compound C4 | 73 |

Referring to the results in Table 2, it may be seen that the organic electroluminescence devices of Examples 1 to 3 exhibited enhanced emission efficiency, when compared with those of Comparative Examples 1 to 4.

It may be seen that the organic electroluminescence devices including a compound having adamantane skeleton exhibited enhanced emission efficiency, when comparing Example 2 with Comparative Example 1.

Furthermore, it may be seen that the organic electroluminescence device of Comparative Example 2 (using a compound having adamantane skeleton without nitrogen therein) exhibited decreased emission efficiency, and that of Comparative Example 3 (using a compound having diamine structure) also exhibited decreased emission efficiency.

An aza-adamantane skeleton has a unique structure in which nitrogen is covered with a substituent having no π electron with an increased steric hindrance, which may have a steric effect of adamantane skeleton and an inductive effect (+I effect) of adamantane skeleton by an alkyl radical. Accordingly, a substructure or a related structure of N-(2-aza-adamantyl)benzene may be a structural unit that inhibits electron transport function by steric protection, and also enhances hole transport function due to inductive effect. The compound of Comparative Example 2 consists of hydrocarbon only and exhibited decreased hole transport function, while the compound of Comparative Example 3 has an arylamine structure and had hole transport function but had no electron transport inhibition function, thereby decreasing the effect of enhancing emission efficiency. Therefore, the effects of enhancing hole transport function and inhibiting electron transport function may play an important role in the material used for a hole transport layer, especially for a hole transport layer disposed adjacent to an emission layer.

According to the above results, it may be seen that the structural unit of aza-adamantane may help inhibit electron transport function due to a steric hindrance by an alkyl radical and also may help enhance hole transport function due to an inductive effect by an alkyl radical, and the organic electroluminescence device including the polycyclic compound according to an embodiment in the hole transport layer may have an increased excitation energy confinement effect on the emission layer, thereby attaining enhanced emission efficiency.

By way of summation and review, in an application of an organic electroluminescence device to a display, decrease of a driving voltage, increase of emission efficiency and extension of life for the organic electroluminescence device may be desirable, and materials which may stably implement these features in the organic electroluminescence device may be considered.

The polycyclic compound according to an embodiment may help improve emission efficiency and life of an organic electroluminescence device.

The organic electroluminescence device according to an embodiment may help attain high efficiency by including the polycyclic compound in a hole transport region, e.g., in a hole transport layer.

The embodiments may provide a polycyclic compound for an organic electroluminescence device with high efficiency.

The embodiments may provide an organic electroluminescence device with high efficiency and long life including a polycyclic compound in a hole transport region.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:
1. A polycyclic compound represented by the following Formula 1:

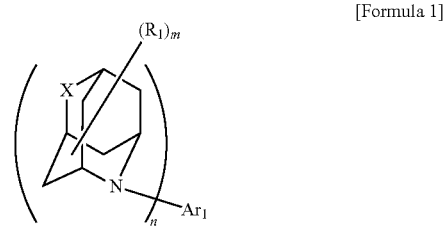

[Formula 1]

wherein, in Formula 1,

X is $CR_2R_3$ or $NAr_2$, $Ar_1$ and $Ar_2$ are each independently a substituted or unsubstituted alkyl group having 1 to 50 carbon atoms, a substituted or unsubstituted aryl group having 6 to 50 ring carbon atoms, a substituted or unsubstituted heteroaryl group having 2 to 50 ring carbon atoms, or a substituted or unsubstituted silyl group, $R_1$ to $R_3$ are each independently a hydrogen atom, a deuterium atom, a halogen atom, a cyano group, a substituted or unsubstituted silyl group, a substituted or unsubstituted alkyl group having 1 to 10 carbon atoms, a substituted or unsubstituted alkoxy group having 1 to 10 carbon atoms, a substituted or unsubstituted arylthio group having 6 to 10 carbon atoms, a substituted or unsubstituted alkylamino group having 1 to 10 carbon atoms, a substituted or unsubstituted arylamino group having 6 to 20 carbon atoms, a substituted or unsubstituted aryl group having 6 to 50 ring carbon atoms, or a substituted or unsubstituted heteroaryl group having 2 to 50 ring carbon atoms, $R_1$ to $R_3$ are separate or form a ring by combining adjacent groups with each other, m is an integer of 0 to 12, and n is an integer of 1 to 3, provided that 1) when m is 0, n is 1, X is $CR_2R_3$ each of $R_2R_3$ is a hydrogen atom, and $Ar_1$ is a substituted phenyl group, a substituent of the substituted phenyl group is selected from the group consisting of deuterium, halogen, nitro, amino, silyl, boron, phosphine oxide, phosphine sulfide, alkyl, alkenyl, alkynyl, aryl and heterocyclic group, 2) when m is 0, n is 1, X is $CR_2R_3$ each of $R_2R_3$ is a hydrogen atom, and $Ar_1$ is a substituted alkyl group, a substituent of the substituted alkyl group is selected from the group consisting of deuterium, halogen, nitro, amino, silyl, boron, phosphine oxide, phosphine sulfide, alkyl, alkenyl, alkynyl, $C_7$-$C_{50}$ aryl, and heterocyclic group,
and 3) when n is 1, and X is $NAr_2$,
$Ar_1$ is a substituted or unsubstituted alkyl group having 2 to 50 carbon atoms, a substituted phenyl group or a substituted or unsubstituted aryl group having 7 to 50 ring carbon atoms, a substituted or unsubstituted heteroaryl group having 2 to 50 ring carbon atoms, or a substituted or unsubstituted silyl group.

2. The polycyclic compound as claimed in claim 1, wherein X is $CR_2R_3$.

3. The polycyclic compound as claimed in claim 1, wherein:
X is $NAr_2$, and
n is 1.

4. The polycyclic compound as claimed in claim 1, wherein the compound represented by Formula 1 is represented by one of the following Formulae 1-1 to 1-4:

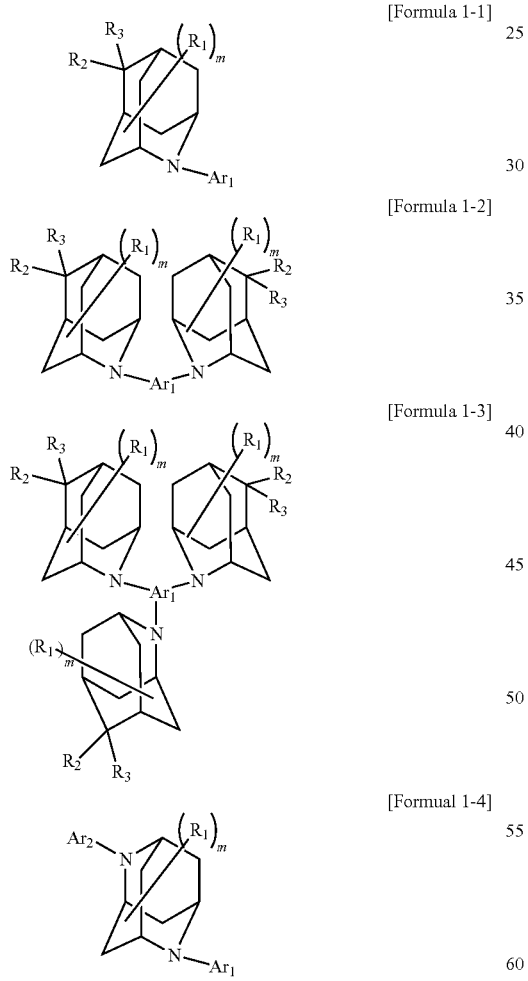

wherein, in Formulae 1-1 to 1-4, $Ar_1$, $Ar_2$, $R_1$ to $R_3$, and m are defined the same as those of Formula 1.

5. The polycyclic compound as claimed in claim 1, wherein the compound represented by Formula 1 is represented by one of the following Formulae 1-5 to 1-7:

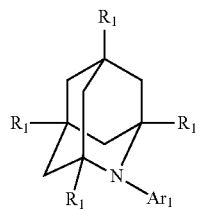
[Formula 1-5]

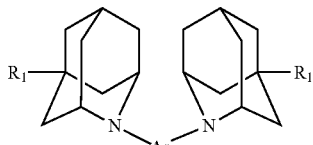
[Formula 1-6]

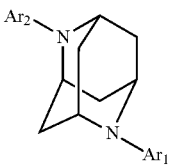
[Formula 1-7]

wherein, in Formulae 1-5 to 1-7, $Ar_1$, $Ar_2$, and $R_1$ are defined the same as those of Formula 1.

6. The polycyclic compound as claimed in claim 1, wherein $Ar_1$ and $Ar_2$ are each independently a substituted or unsubstituted phenyl group, a substituted or unsubstituted biphenyl group, a substituted or unsubstituted terphenyl group, a substituted or unsubstituted heteroaryl group including O, S or N as a heteroatom, or a substituted or unsubstituted silyl group.

7. The polycyclic compound as claimed in claim 1, wherein: n is 1, and
$Ar_1$ is a group represented by one of the following Ar-1 to Ar-8:

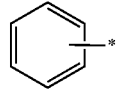
Ar-1

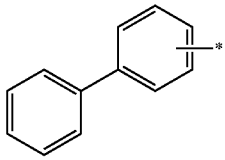
Ar-2

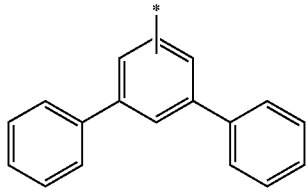
Ar-3

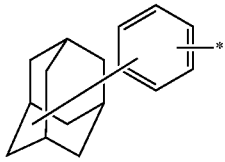
Ar-4

-continued

Ar-5
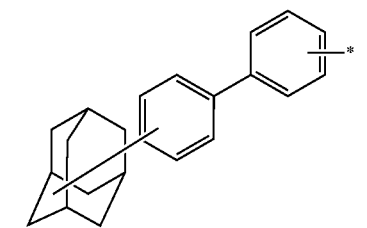

Ar-6
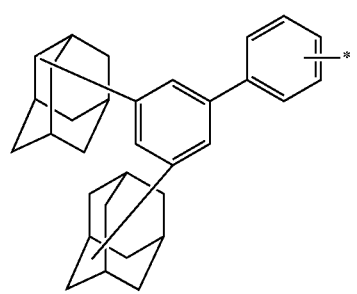

Ar-7
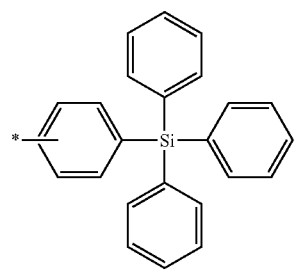

Ar-8
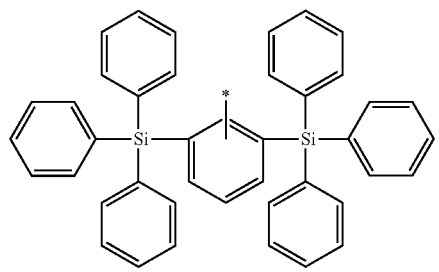

wherein in Ar-1 to Ar-8, -* represents a bonding site to another atom.

8. The polycyclic compound as claimed in claim 1, wherein: n is 1,
Ar₁ is a group represented by one of the following Ar-9 to Ar-11:

Ar-9
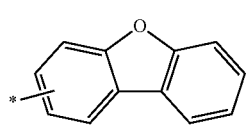

Ar-10
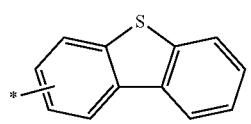

-continued

Ar-11
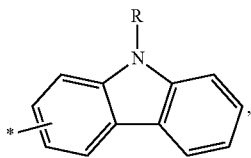

in Ar-11, R is a substituted or unsubstituted aryl group having 6 to 50 ring carbon atoms, and
wherein in Ar-9 to Ar-11, -* represents a bonding site to another atom.

9. The polycyclic compound as claimed in claim 1, wherein: n is 2, and
Ar₁ is a group represented by one of the following Ar-12 to Ar-16:

Ar-12
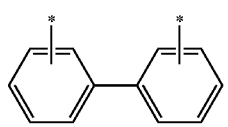

Ar-13
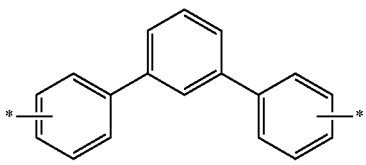

Ar-14
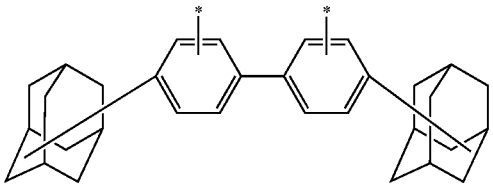

Ar-15
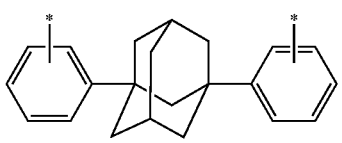

Ar-16
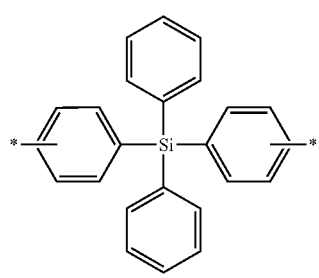

wherein in Ar-12 to Ar-16, -* represents a bonding site to another atom.

10. The polycyclic compound as claimed in claim 1, wherein Ar₂ is a substituted or unsubstituted triphenylsilyl group.

11. The polycyclic compound as claimed in claim 1, wherein R₁ is a substituted or unsubstituted phenyl group or a substituted or unsubstituted methyl group.

12. The polycyclic compound as claimed in claim 1, wherein the compound represented by Formula 1 is a compound of the following Compound Group

[Compound Group 1]
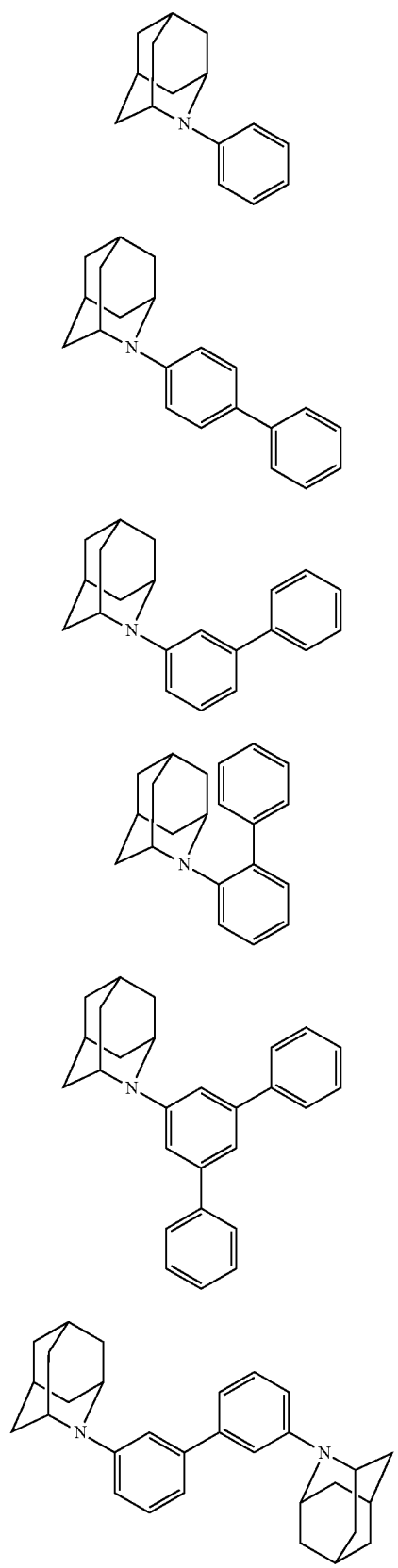
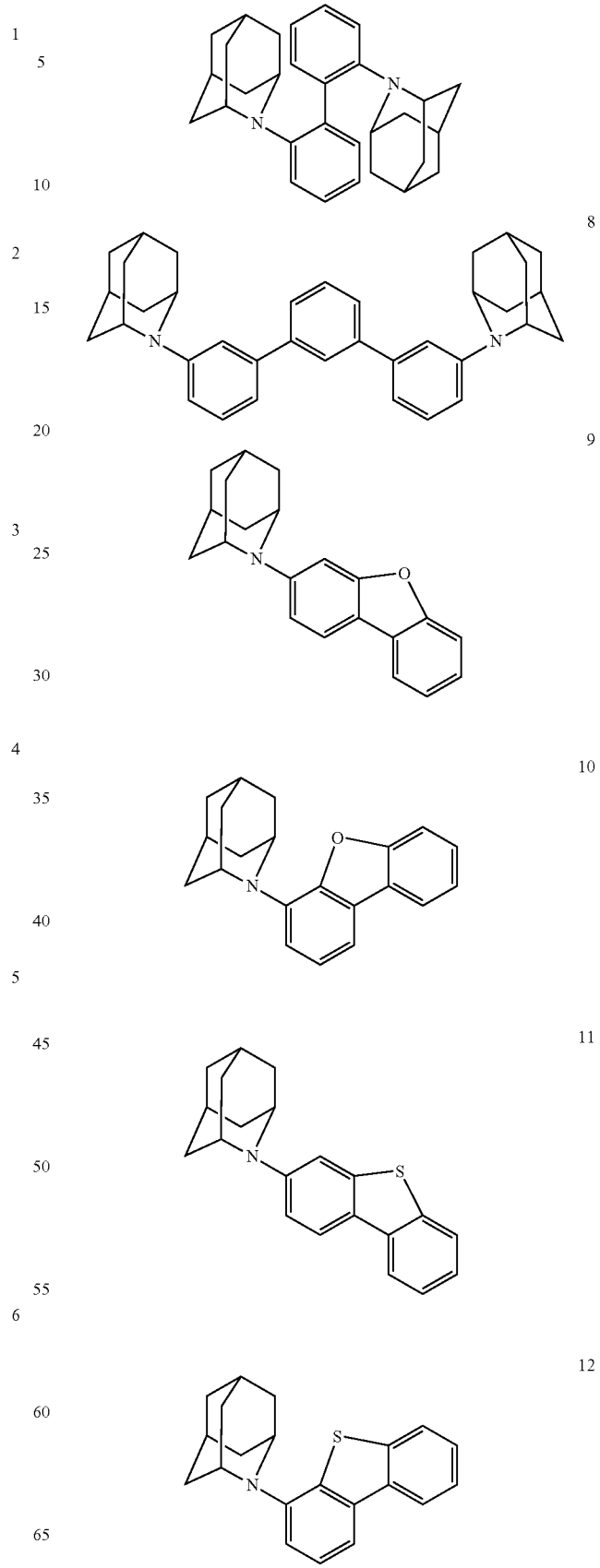

13
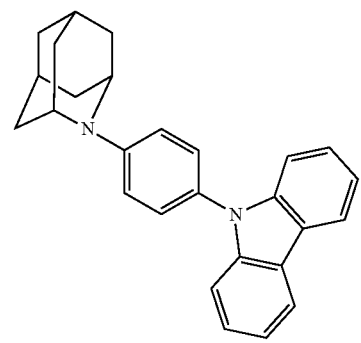
14
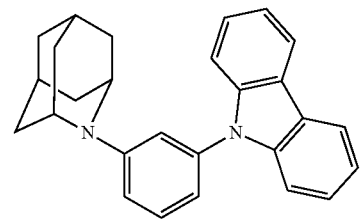
15
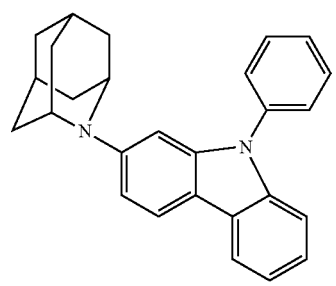
16
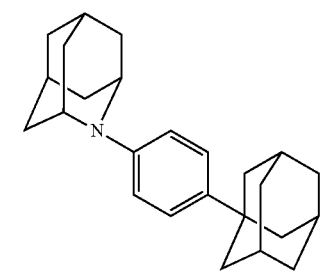
17
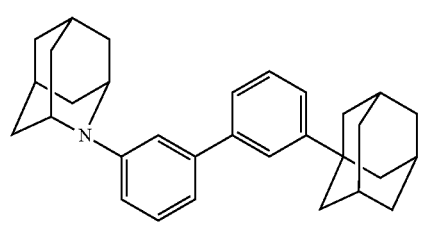
18
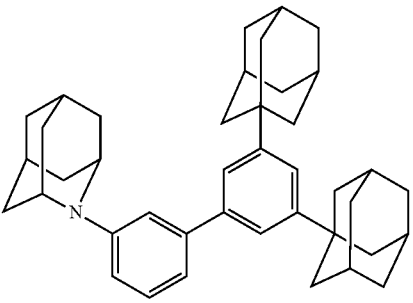
19
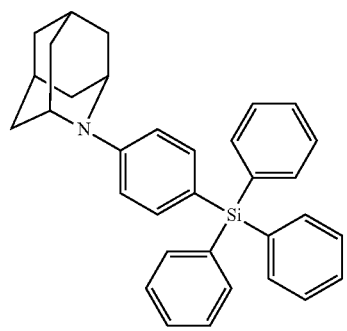
20
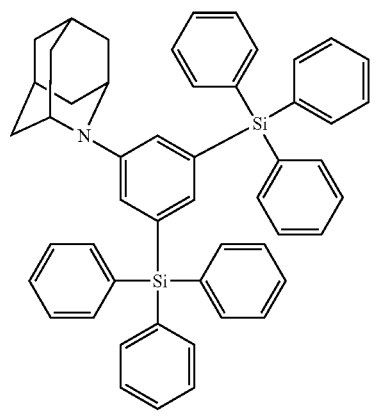
21
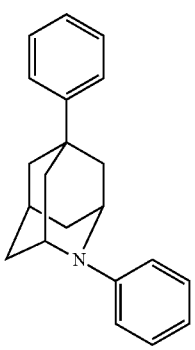

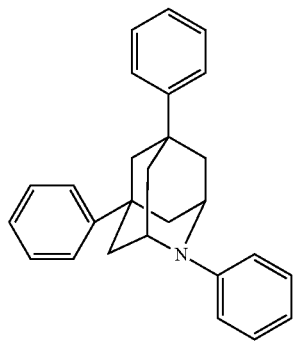
22
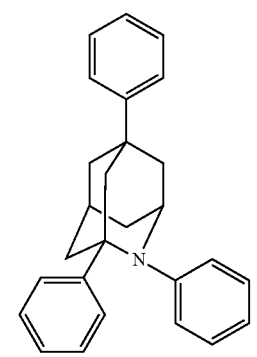
23
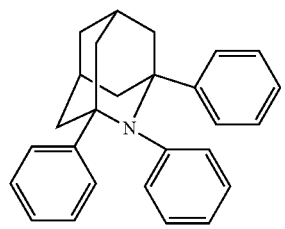
24
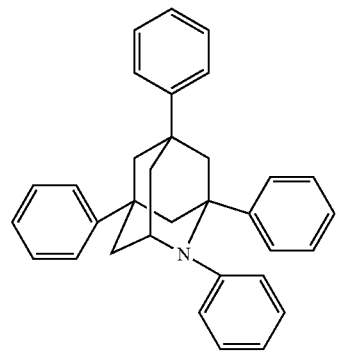
25
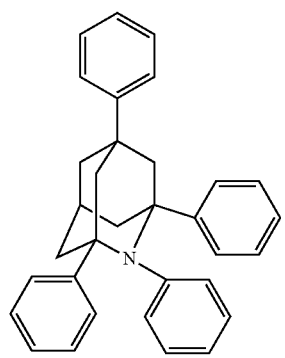
26
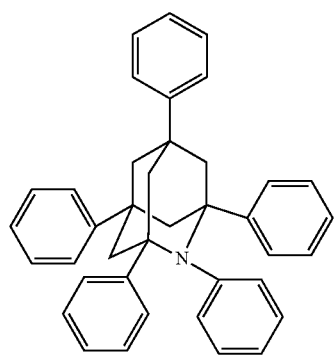
27
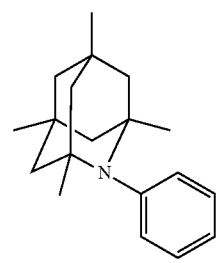
28
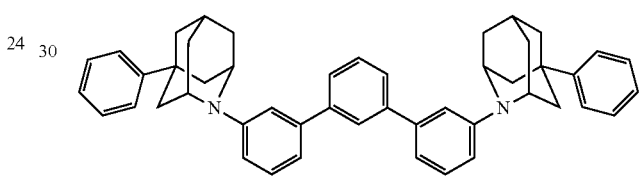
29
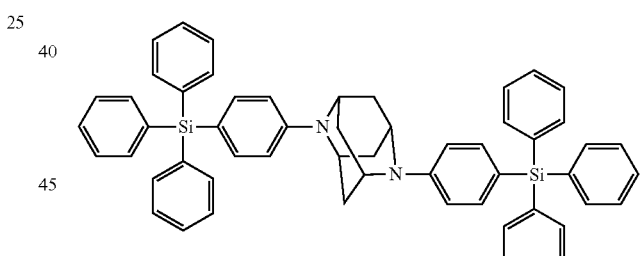
30
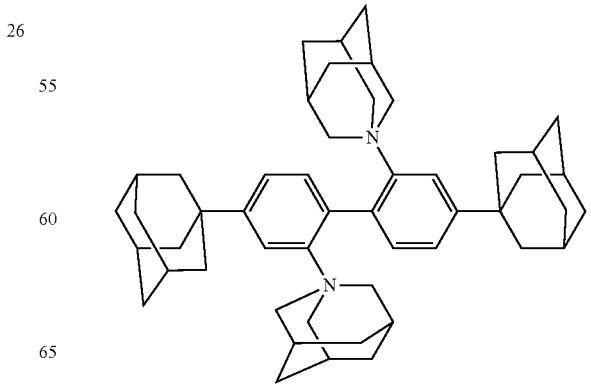
31

-continued

32

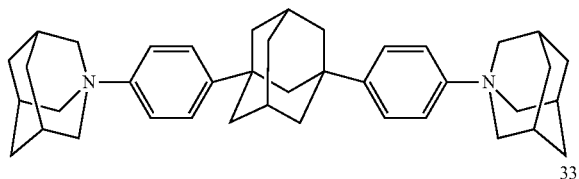

33

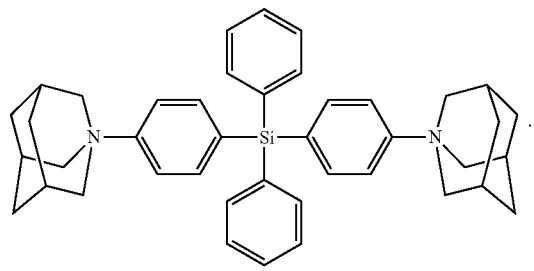

13. An organic electroluminescence device, comprising:
a first electrode;
a hole transport region on the first electrode;
an emission layer on the hole transport region;
an electron transport region on the emission layer; and
a second electrode on the electron transport region,
wherein the hole transport region includes a polycyclic compound represented by the following Formula 1:

[Formula 1]

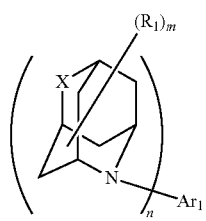

wherein, in Formula 1,

X is $CR_2R_3$ or $NAr_2$, $Ar_1$ and $Ar_2$ are each independently a substituted or unsubstituted alkyl group having 1 to 50 carbon atoms, a substituted or unsubstituted aryl group having 6 to 50 ring carbon atoms, a substituted or unsubstituted heteroaryl group having 2 to 50 ring carbon atoms, or a substituted or unsubstituted silyl group, $R_1$ to $R_3$ are each independently a hydrogen atom, a deuterium atom, a halogen atom, a cyano group, a substituted or unsubstituted silyl group, a substituted or unsubstituted alkyl group having 1 to 10 carbon atoms, a substituted or unsubstituted alkoxy group having 1 to 10 carbon atoms, a substituted or unsubstituted arylthio group having 6 to 10 carbon atoms, a substituted or unsubstituted alkylamino group having 1 to 10 carbon atoms, a substituted or unsubstituted arylamino group having 6 to 20 carbon atoms, a substituted or unsubstituted aryl group having 6 to 50 ring carbon atoms, or a substituted or unsubstituted heteroaryl group having 2 to 50 ring carbon atoms, $R_1$ to $R_3$ are separate or form a ring by combining adjacent groups with each other, m is an integer of 0 to 12, and n is an integer of 1 to 3.

14. The organic electroluminescence device as claimed in claim 13, wherein:

the hole transport region includes:
a hole injection layer; and
a hole transport layer between the hole injection layer and the emission layer, and the hole transport layer includes the polycyclic compound represented by Formula 1.

15. The organic electroluminescence device as claimed in claim 13, wherein the emission layer emits blue light.

16. The organic electroluminescence device as claimed in claim 13, wherein the compound represented by Formula 1 is represented by one of the following Formulae 1-1 to 1-4:

[Formula 1-1]

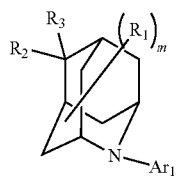

[Formula 1-2]

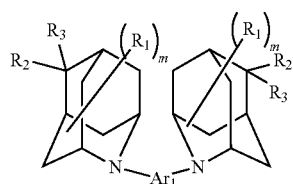

[Formula 1-3]

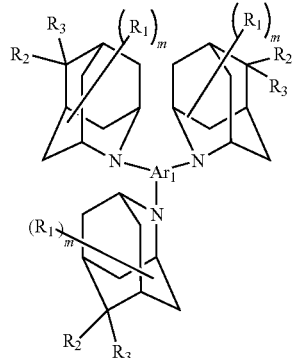

[Formual 1-4]

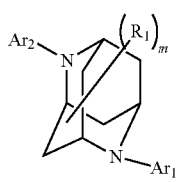

wherein, in Formulae 1-1 to 1-4, $Ar_1$, $Ar_2$, $R_1$ to $R_3$, and m are defined the same as those of Formula 1.

17. The organic electroluminescence device as claimed in claim 13, wherein the compound represented by Formula 1 is represented by one of the following Formulae 1-5 to 1-7:

[Formula 1-5]

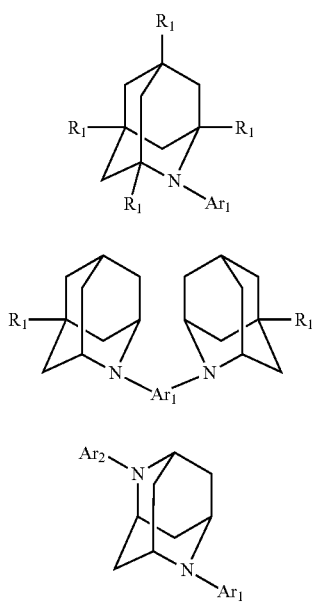

[Formula 1-6]

[Formula 1-7]

wherein, in Formulae 1-5 to 1-7, $Ar_1$, $Ar_2$, and $R_1$ are defined the same as those of Formula 1.

18. The organic electroluminescence device as claimed in claim 13, wherein: n is 1, $Ar_1$ is a group represented by one of the following Ar-1 to Ar-11:

Ar-1, Ar-2, Ar-3, Ar-4

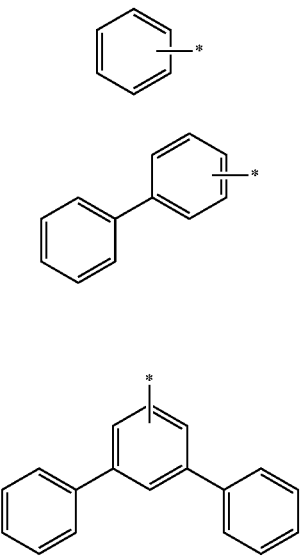

Ar-5, Ar-6

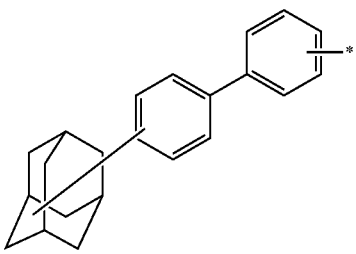

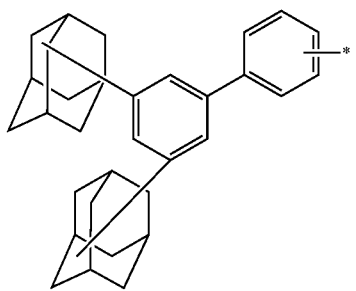

Ar-7

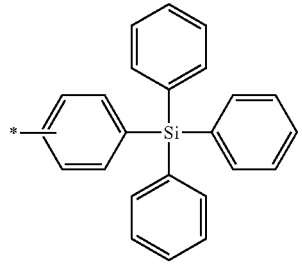

Ar-7

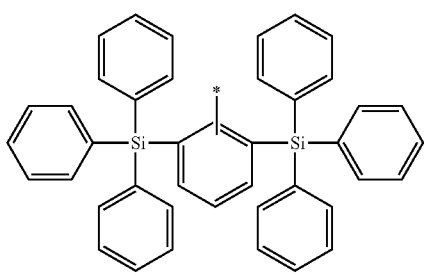

Ar-9

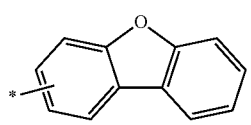

Ar-10, Ar-11

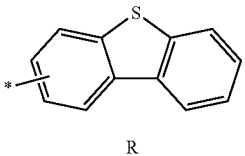

in Ar-11, R is a substituted or unsubstituted aryl group having 6 to 50 ring carbon atoms, and wherein in Ar-1 to Ar-11, -* represents a bonding site to another atom.

19. The organic electroluminescence device as claimed in claim 13, wherein:
n is 2, and
$Ar_1$ is a group represented by one of the following Ar-12 to Ar-16:

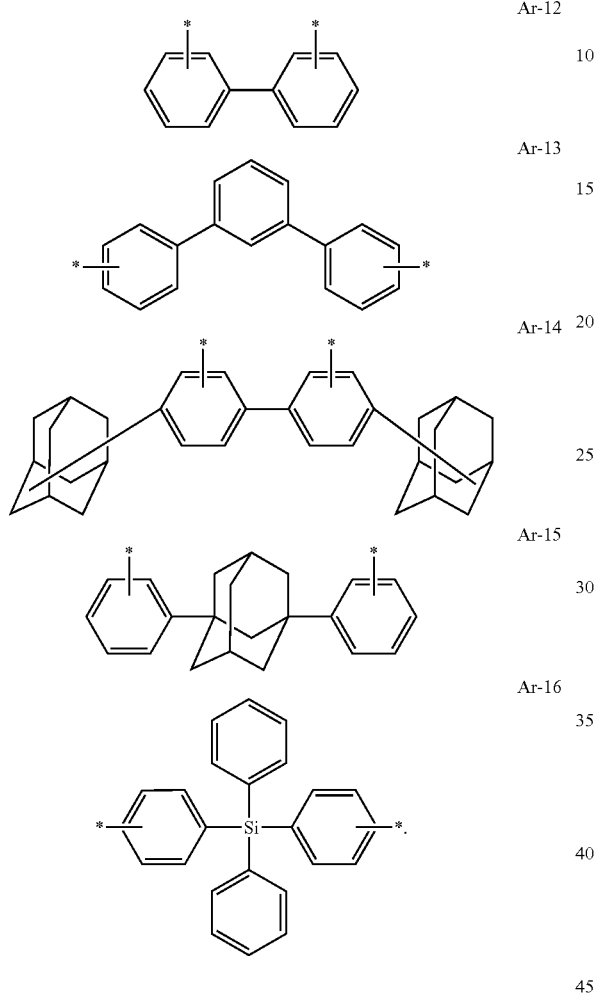

wherein in Ar-12 to Ar-16, -* represents a bonding site to another atom.

20. The organic electroluminescence device as claimed in claim 13, wherein:
the hole transport region includes the compound represented by Formula 1, and
the compound represented by Formula 1 is a compound of the following Compound Group 1:

[Compound Group 1]

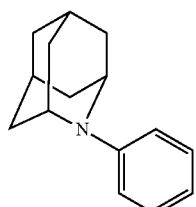

1

-continued

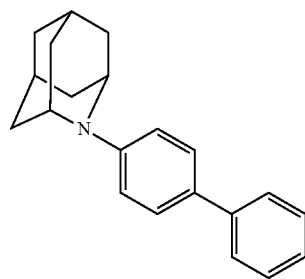

2

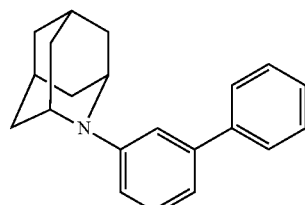

3

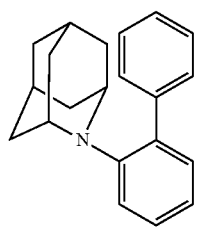

4

5

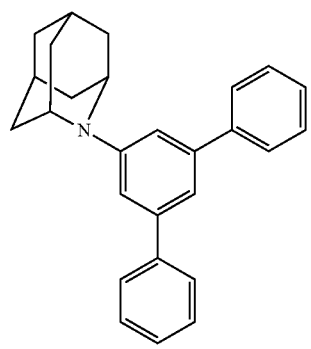

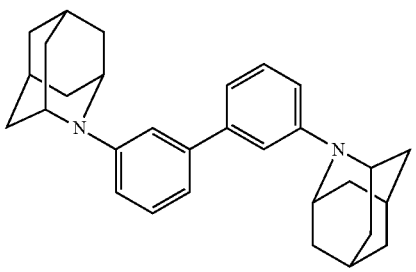

6

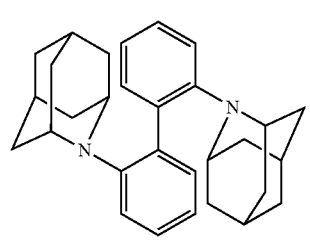

7

8
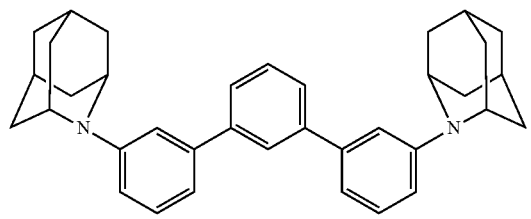
9
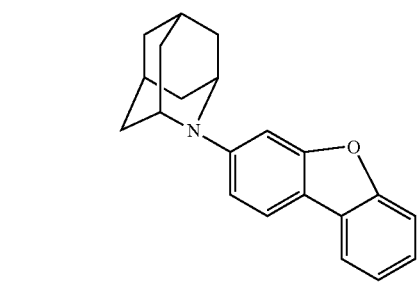
10
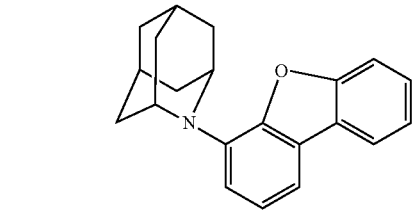
11
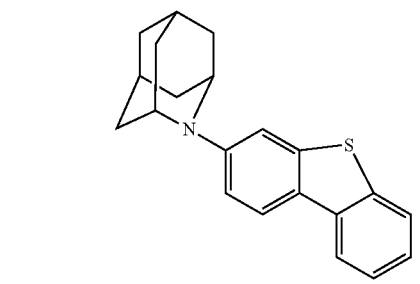
12
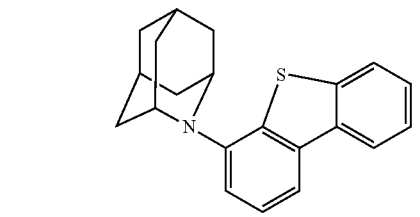
13
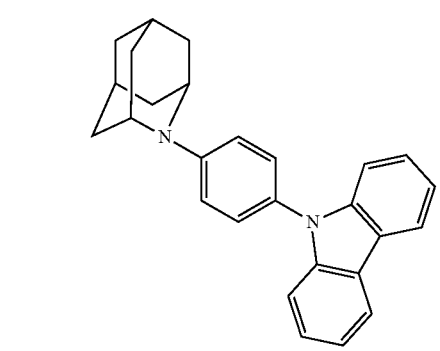
14
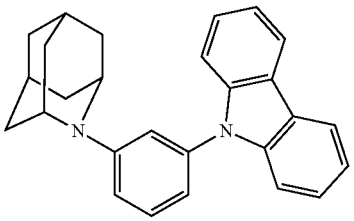
15
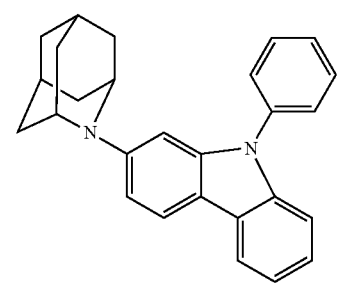
16
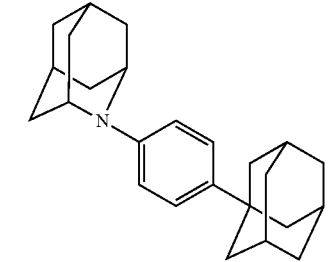
17
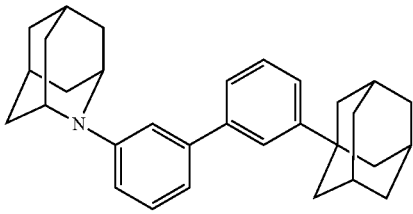
18
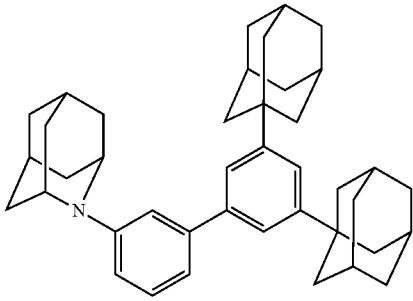
19
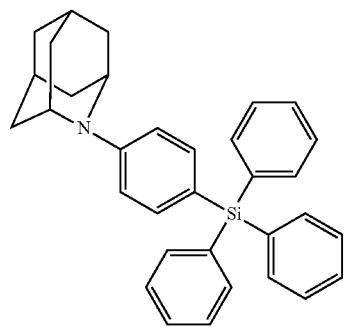

20
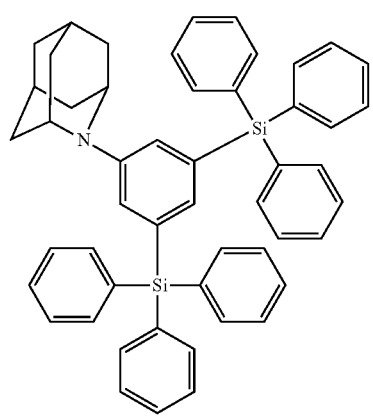
21
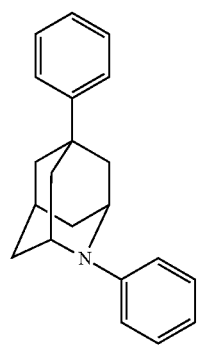
22
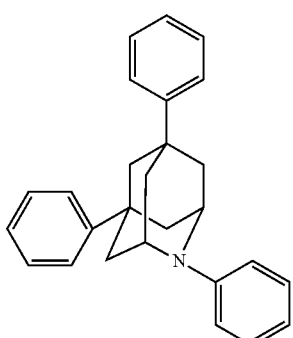
23
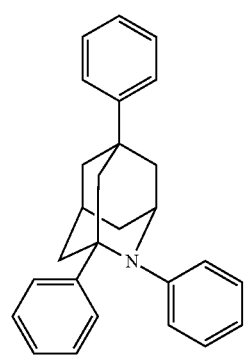
24
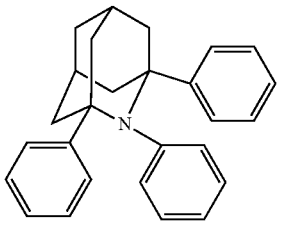
25
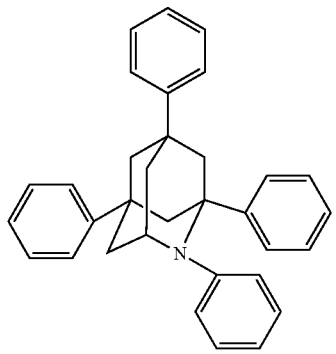
26
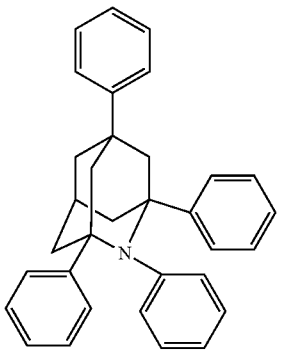
27
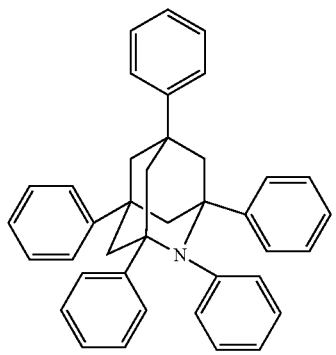

-continued
28
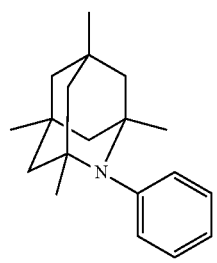
29
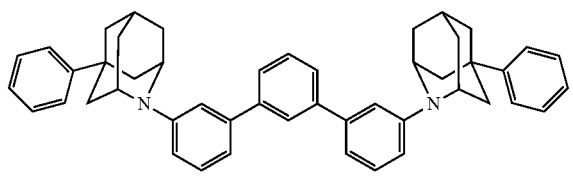
30
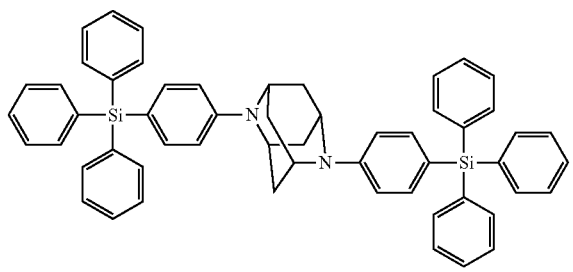
-continued
31
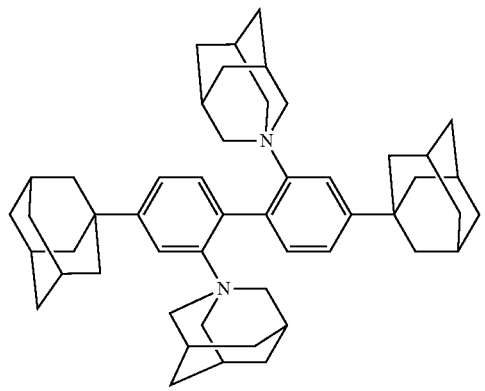
32
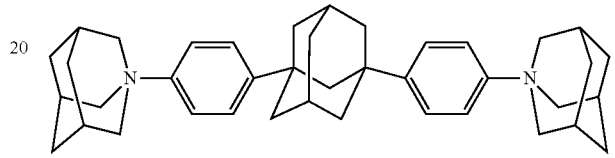
33
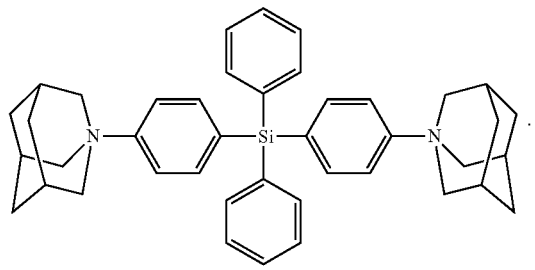
* * * * *

UNITED STATES PATENT AND TRADEMARK OFFICE
CERTIFICATE OF CORRECTION

PATENT NO. : 10,910,578 B2
APPLICATION NO. : 16/032215
DATED : February 2, 2021
INVENTOR(S) : Ichinori Takada et al.

It is certified that error appears in the above-identified patent and that said Letters Patent is hereby corrected as shown below:

In the Specification

In Column 11, Lines 51-66 (approx.), delete " 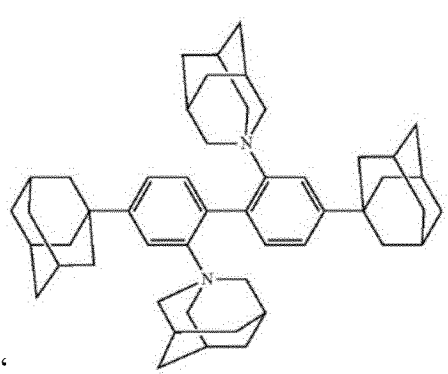 " and insert -- 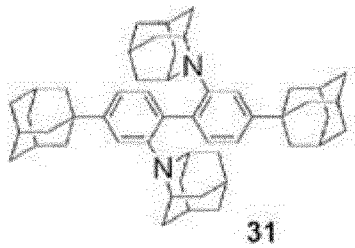 --

In Column 12, Lines 3-9 (approx.), delete " 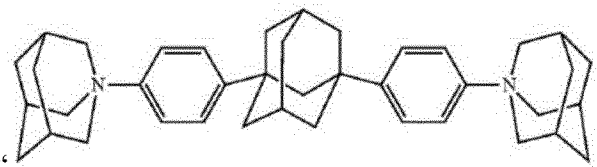 " and

Signed and Sealed this
Twenty-seventh Day of July, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,910,578 B2

insert -- --

In Column 12, Lines 10-20 (approx.), delete " 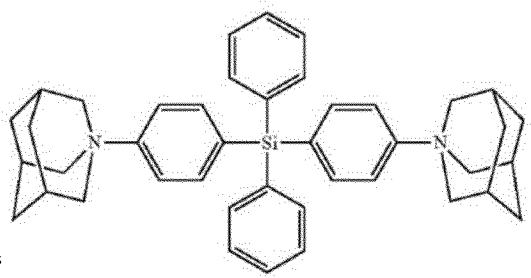 " and

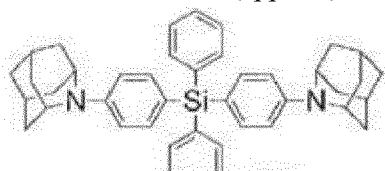

insert -- --

In Column 22, Lines 3-16 (approx.), delete " 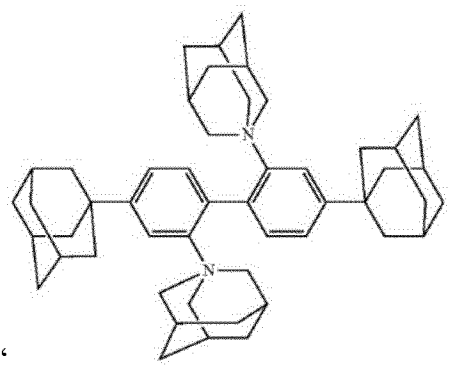 " and insert

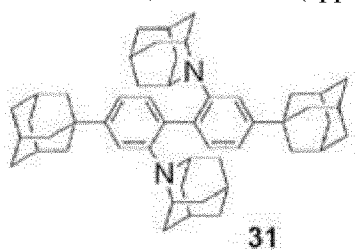

-- --

In Column 22, Lines 17-24 (approx.), delete " 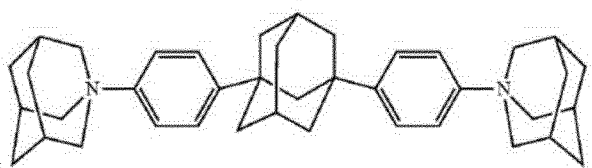 " and

CERTIFICATE OF CORRECTION (continued)
U.S. Pat. No. 10,910,578 B2 insert --  32 --

In Column 22, Lines 25-36 (approx.), delete " 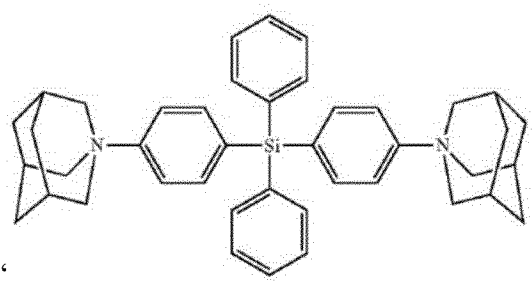 " and insert -- 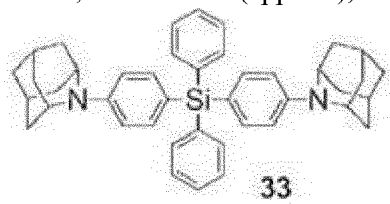 --

In Column 35, Lines 21-36 (approx.), delete " 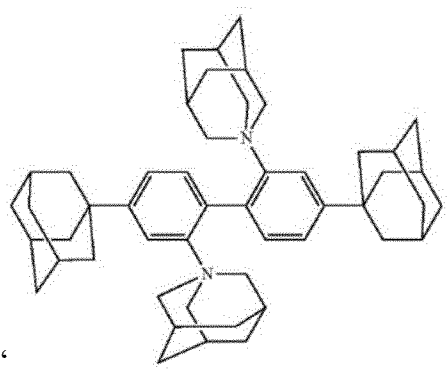 " and insert

-- 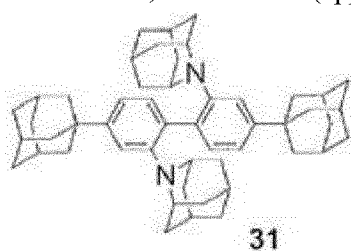 31 --

In Column 35, Lines 36-43 (approx.), delete " 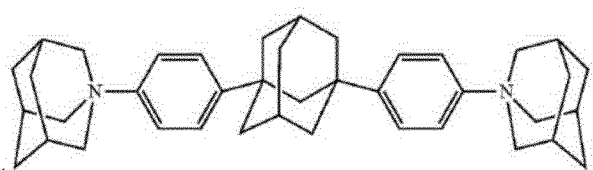 " and insert --  --
In Column 35, Lines 44-54 (approx.), delete " 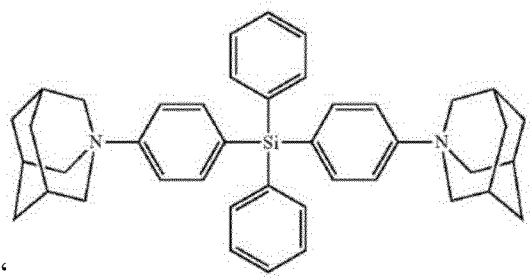 " and insert -- 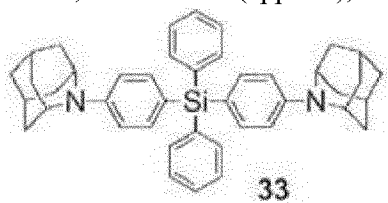 --
In Column 45, Lines 21-35 (approx.), delete " 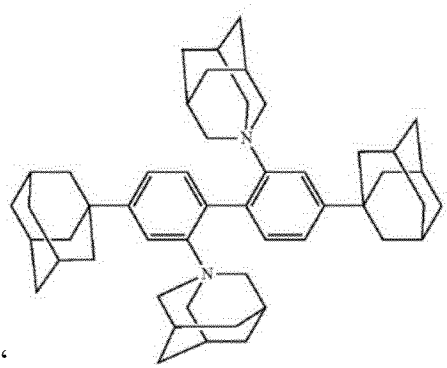 " and insert -- 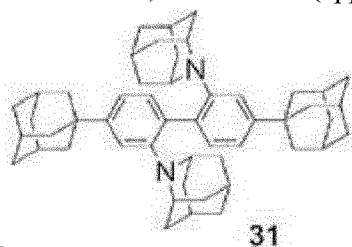 --

CERTIFICATE OF CORRECTION (continued)
U.S. Pat. No. 10,910,578 B2

In Column 45, Lines 36-43 (approx.), delete " 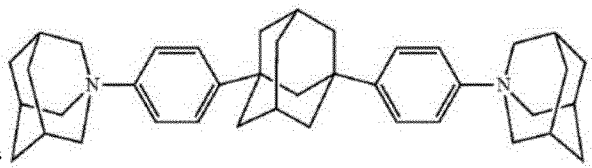 " and insert --  --

In Column 45, Lines 44-54 (approx.), delete " 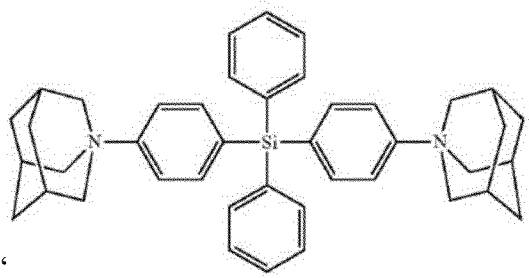 " and insert -- 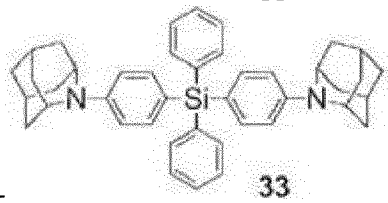 --

In the Claims

In Column 66, Lines 52-66 (approx.), In Claim 12, delete

" 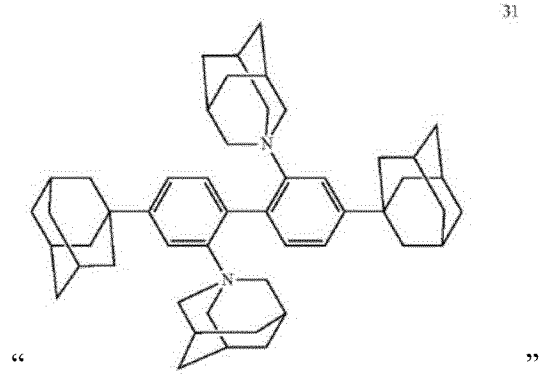 "

and insert -- 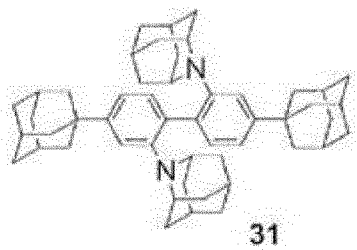 --
In Column 67, Lines 2-8 (approx.), In Claim 12, delete " 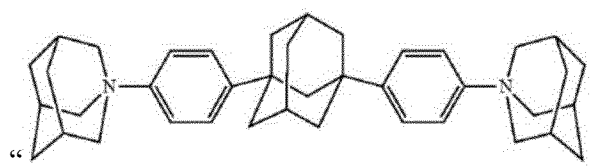 " and insert -- 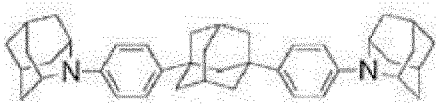 --
In Column 67, Lines 9-20 (approx.), In Claim 12, delete " 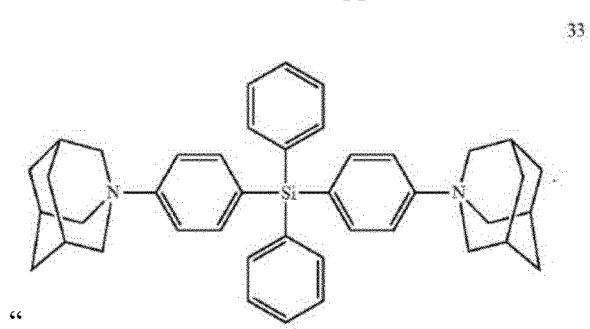 " and insert -- 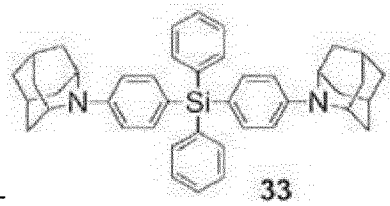 --
In Column 78, Lines 3-17 (approx.), In Claim 20, delete " 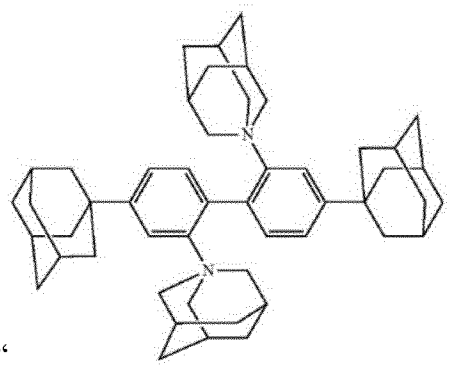 "
and insert -- 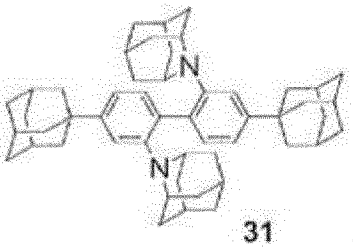 --
In Column 78, Lines 18-24 (approx.), In Claim 20, delete "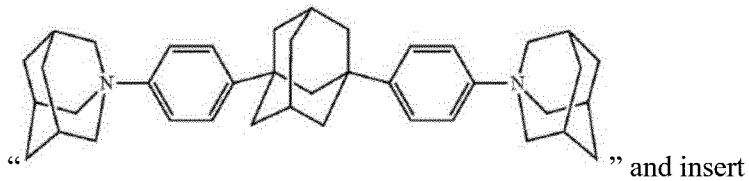 and insert
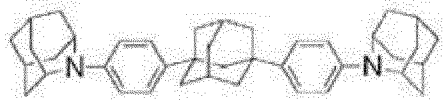 --
In Column 78, Lines 25-35 (approx.), In Claim 20, delete
"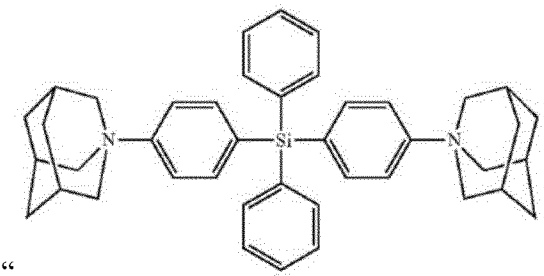" and insert -- 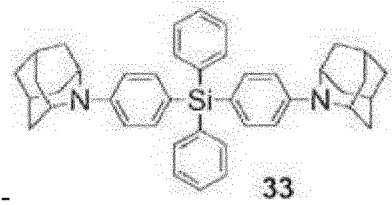 --